US006576419B1

(12) United States Patent
Wei et al.

(10) Patent No.: US 6,576,419 B1
(45) Date of Patent: Jun. 10, 2003

(54) ASSAY PROCEDURE USING FLUOROGENIC TRACERS

(75) Inventors: Ai-Ping Wei, Woodbury, MN (US); James N. Herron, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 08/891,114

(22) Filed: Jul. 10, 1997

Related U.S. Application Data

(63) Continuation of application No. 08/484,563, filed on Jun. 7, 1995, now abandoned, and a continuation-in-part of application No. 08/096,338, filed on Jul. 23, 1993.

(30) Foreign Application Priority Data

Jul. 22, 1994 (WO) ................................ PCT/0594/08279

(51) Int. Cl.⁷ ............................ C12Q 1/08; C12P 19/34; C07H 21/02
(52) U.S. Cl. ......................... 435/6; 435/91.1; 435/91.2; 435/91.3; 435/91.5; 536/23.1; 536/24.3; 536/24.31; 536/24.32; 536/24.33
(58) Field of Search ..................... 435/6, 91.2, 91.3, 435/91.5, 91.1; 536/24.3, 23.1, 24.31, 24.32, 24.33

(56) References Cited

U.S. PATENT DOCUMENTS

| | | | |
|---|---|---|---|
| 4,220,450 A | 9/1980 | Maggio | 23/230 B |
| 4,261,968 A | 4/1981 | Ullman et al. | 424/8 |
| 4,318,981 A | 3/1982 | Burd et al. | 435/7 |
| 4,681,859 A | 7/1987 | Kramer | 436/501 |
| 4,777,128 A | 10/1988 | Lippa | 435/5 |
| 4,833,092 A | 5/1989 | Geysen | 436/501 |
| 4,868,103 A | 9/1989 | Stavrianopoulos et al. | 435/5 |
| 4,975,380 A | 12/1990 | Hummelen et al. | 436/546 |
| 4,996,143 A | 2/1991 | Heller et al. | 435/6 |
| 5,037,615 A | 8/1991 | Kane | 422/82.08 |
| 5,070,025 A | 12/1991 | Klein et al. | 436/546 |
| 5,237,515 A | 8/1993 | Herron et al. | 364/498 |
| 5,326,692 A | 7/1994 | Brinkley et al. | 435/6 |
| 5,538,848 A * | 7/1996 | Livak et al. | 435/5 |

FOREIGN PATENT DOCUMENTS

| | | |
|---|---|---|
| EP | 0 331 126 A2 | 9/1969 |
| EP | 0 070 685 | 1/1983 |
| EP | 0 137 515 | 4/1985 |
| GB | 2 223 096 | 3/1990 |
| WO | WO 87/07385 | 12/1987 |
| WO | WO 92/00388 | 1/1992 |

OTHER PUBLICATIONS

Parkhurst et al, "Kinetic studies by fluorescence resonance energy transfer employing a double–labeled oligonucleotide: hybridization to the oligonucleotide complement and to single stranded DNA", Biochemistry 34:285–292, Jan. 1995.*

Parkhurst et al, "Kinetic studies of oligonucleotide DNA hybridization in solution by fluorescence resonance energy transfer", Abstracts Biophysical Journal 64(2):A266. Feb. 1993.*

*Aguirresacona et al., "Spectroscopic and Thermodynamic Study on the Aggregation of Rhodamines in Solution", *Journal of Chemical Eduction,* vol. 66, No. 10, pp. 866–869, Oct. 1989.

*Arbeloa et al., "Dimeric States of Rhodamine B", *Chemical Physics Letters,* vol. 87, No. 6, pp. 556–560, Apr., 1982.

Bailey et al., "On the use of fluorescent labels in immunoassay", *J. Pharm. & Biomed. Anal.,* vol. 5, No. 7, pp. 649–658, 1987.

*Barnard et al., "Chemical Sensors Based on Controlled–Release Polymer Systems", *Science,* vol. 25, pp. 927–929, Feb. 22, 1991.

*Bates et al., "Comparative Properties of Monoclonal Antibodies Comprising a High–Affinity Anti–Fluorescyl Idiotype Family", *Molecular Immunology,* vol. 22, No. 8, pp. 871–877, 1985.

*Bird et al., "Single–Chain Antigen–Binding Proteins", *Science,* vol. 242, pp. 423–426, Oct. 21, 1988.

Carlsen et al., "Human Chorionic Gonadotropin Linear Amino Acid Sequence of the β Subunit", *J. Biol. Chem.,* vol. 248, No. 19, pp. 6810–6827, 1973.

*Edmundson et al., "A Search For Site–Filling Ligands in the Mcg Bence–Jones Dimer: Crystal Binding Studies of Fluorescent Compounds", *Molecular Immunology,* vol. 21, No. 7, pp. 561–576, 1984.

*Farkas et al., "Fluorescence properties of bichromophoric molecules", *Spectrochimica,* vol. 48A, No. 1, pp. 95–99, 1992.

(List continued on next page.)

*Primary Examiner*—Jeffrey Fredman
(74) *Attorney, Agent, or Firm*—TraskBritt

(57) ABSTRACT

Fluorescent energy transfer dyes capable of moving between a more stacked configuration to exhibit fluorescent quenching and a more spaced configuration to exhibit fluorescence can be conjugated to a peptide epitope or nucleic acid for use in the detection of an unknown antibody in bulk solution. The resulting labeled peptide reagent can be used in an immunoassay procedure by placing it in bulk solution along with the unknown antibody to be detected. When the antibody binds to the peptide epitope, the pair of dyes carried by the peptide epitope will have their configuration altered from a stacked to an unstacked configuration and will exhibit a fluorescent increase in response thereto.

7 Claims, 15 Drawing Sheets

OTHER PUBLICATIONS

Gosling, James P., "A Decade of Development in Immunoassay Methodology", *Clinical Chemistry*, vol. 36, No. 8, pp. 1408–1427, 1990.

*Haas et al., "Distribution of End–to–End Distances of Oligopeptides in Solution as Estimated by Energy Transfer", *Proc. Natl. Acad. Sci USA*, vol. 72, No. 5, pp. 1807–1811, May 1975.

*Herman et al., "Dynamics and Topographical Distribution of Surface Glycoproteins during Myoblast Fusion: A Resonance Energy Transfer Study", *Biochemistry*, vol. 21, No. 14, pp. 3275–3283, 1982.

Herron, J.N., *Fluorescein Hapten: An Immunological Probe*, J.E.W. Voss, Eds., (CRC Press, 1981), pp. 53–55.

Herron et al., "Three–Dimensional Structure of a Fluorescein–Fab Complex Crystallized in 2–Methyl-2, 4–pentanediol", *Proteins: Structure, Function, and Genetics*, 5:271–280, 1989.

Hlady et al., "Total Internal Reflection Intrinsic Fluorescence (TIRIF) spectroscopy Applied to Protein Adsorption", *Surface and Interfacial Aspects of Biomedical Polymers: Protein Adsorption*, J.D. Andrade, Ed. (Plenum Press, New York, NY), pp. 81–119, 1985.

*Jiskoot et al., "Preparation and Application of a Fluorescein–Labeled Peptide for Determining the Affinity Constant of a Monoclonal Antibody–Hapten Complex by Fluorescence Polarization", *Analytical Biochemistry*, 196, pp. 421–426, 1991.

*Katchalski–Katzir et al., "Study of Conformation and Intramolecular Motility of Polypeptides in Solution by a Novel Fluorescence Method", *Annals New York Academy of Sciences*, pp. 44–61, 1981.

*Kranz et al., "Kinetics and Mechanism of Deuterium Oxide–induced Fluorescence Enhancement of Fluorescyl Ligand Bound to Specific Heterogeneous and Homogeneous Antibodies", *The Journal of Biological Chemistry*, vol. 256, No. 9, Issue of May 10, pp. 4433–4438, 1981.

*Kranz et al., "Partical Educidation of An Anti–Hapten Repertoire in Balb/c MICE: Comparative Characterization of Several Monoclonal Anti–Fluorescyl Antibodies", *Molecular Immunology*, vol. 18, No. 10, pp. 889–898, 1981.

*Matayoshi et al., "Novel Fluorogenic Substrates for Assaying Retroviral Proteases by Resonance Energy Transfer", *Science*, vol. 247, pp. 954–958, Feb., 1990.

*Morrison et al., "Solution–Phase Detection of Polynucleotides Using Interacting Fluorescent Labels and Competitive Hybridization", *Analytical Biochemistry*, vol. 183, pp. 231–244, 1989.

Nithipatikom et al, "Homogeneous Immunochemical Technique for Determination of Human Lactoferrin Using Excitation Transfer and Phase–Resolved Fluorometry", *Anal. Chem.*, 59:423–427, 1987.

*Patel et al "A 'homogeneous' immunoassay method for cyclic AMP involving the use of chemilunisence–energy transfer", *Biochemical Society Transations*, vol. 11, pp. 196–197, 1983.

*Rohatgi et al., "Aggregation Properties of Anions of Fluorescein and Halofluorescein Dyes*", *J. Indian Chem. Soc.*, vol. 49, No. 12, pp. 1311–1320, 1972.

Scott et al., "Searching for Peptide Ligands with an Epitope Library", *Science*, vol. 249, pp. 386–390, 1990.

*Stryer et al., "Energy Transfer: A Spectroscopic Ruler", *Biochemistry Proc. N.A.S.*, vol. 58, pp. 719–726, 1967.

Tampe et al., "Energy Transfer Between Two Peptides Bound to One MHC Class II Molecule", *Reports*, vol. 254, pp. 87–90, Oct., 1991.

*Ullman et al., "Fluorescent Excitation Transfer Immunoassay A General Method for Determination of Antigens", *The Journal of Biological Chemistry* vol. 251, No. 14, Issue of Jul. 25, pp. 4172–4178, 1976.

*Ullman et al., "Fluorescence Excitation Transfer Immunoassay (FETI)", *Methods in Enzymology*, vol. 74, pp. 28–60, 1981.

van Erp et al., "Affinity of monoclonal antibodies Interpretation of the positive cooperative nature of anti–hCG/hCG interactions", *J. Immunol. Methods*, 140:235–241, 1991.

*Wei et al., "Characterization of Fluorescent Dyes for Optical Immunosensors Based on Fluorescence Energy Transfer", *Biosensor Design and Application*, pp. 105–120, 1992.

*Ai–Ping Wei et al., "Fluorescence Polarization Immunoassay of High Molecular Weight Antigens", to be submitted to *Analytical Biochemistry*, pp. 1–27, May, 1992.

*Wenska G., "Bichromophoric Compounds As Chemical Models In The Study of the Photochemistry of Nucleic Acids", *Journal of Photochemistry and Photobiology, A: Chemistry*, 49, pp. 167–185, 1989.

*West et al., "The Dimeric State of Cyanine Dyes", *The Journal of Physical Chemistry*, vol. 69, No. 6, pp. 1894–1903, Jun., 1965.

Arbeloa, I. Lopez, "Dimeric and Timeric States of the Fluorescein Dianion Part 1.—Molecular Structures", *J. Chem. Soc.*, Faraday Trans. 2, 77, pp. 1725–1733, 1981.

Arbeloa, I. Lopez, "Dimeric and Trimeric States of the Fluorescein Dianion Part 2.—Effects on Fluorescence Characteristics", *J. Chem. Soc.*, Faraday Trans., 2, 77, pp. 1735–1742, 1981.

Barbas et al., "Semisynthetic Combinatorial antibody libraries: A chemical solution to the diversity problem", *Proc. Natl. Acad. Sci. USA*, vol. 89, pp. 4457–4461, May 1992.

Bellisario et al., "Human Chorionic Gonadotropin", *The Journal of Biological Chemistry*, vol. 248, No. 19, pp. 6796–6809, 1973.

Burd et al., "Homogeneous Reactant–Labeled Fluorescent Immunoassay for Therapeutic Drugs Exemplified by Gentamicin Determination in Human Serum", *Clin. Chem.*, vol. 23, No. 8, pp. 1402–1408, 1977.

Diamandis, E., "Multiple Labeling and Time–Resolvable Fluorophores", *Clin. Chem.*, vol. 37, No. 9, pp. 1486–1491, 1991.

Geysen et al., "A Priori Delineation of A Peptide Which Mimics A Discontinuous Antigenic Determinant", *Molecular Immunology*, vol. 23, No. 7, pp. 709–715, 1986.

Houghton et al., "Generation and use of synthetic peptide combinatorial libraries for basic research and drug discovery", *Nature*, vol. 354, pp. 84–86, Nov. 1991.

Jolley et al., "Fluorescence Polarization Immunoassay 1. Monitoring Aminoglycoside Antibiotics in Serum and Plasma", *Clinical Chemistry*, vol. 27, No. 7, pp. 1190–1197, 1981.

Lam et al., "A new type of synthetic peptide library for identifying ligand–binding activity", *Nature*, vol. 354, pp. 82–84, Nov. 1991.

Lerner et al., Antibodies Without Immunization, *Science*, vol. 258, pp. 1313–1314, Nov. 1992.

Marks et al., "Molecular Evolution of Proteins on Filamentous Phage", *The Journal of Biological Chemistry*, vol. 267, No. 23, pp. 16007–16010, Aug. 1992.

Merrifield et al., "Solid Phase Peptide Synthesis. I. The Synthesis of a Tetrapeptide", pp. 2149–2154, Jul. 20, 1963.

Morris et al., "Flavin Adenine Dinucleotide as a Label in Homogeneous Colorimetric Immunoassays", *Anal. Chem.*, vol. 53, No. 4, pp. 658–665, 1981.

Rohatgi et al., "Nature of Bonding in Dye Aggregates", *The Journal of Physical Chemistry*, vol. 70, No. 6, pp. 1695–1701, Jun. 1966.

Rohatgi et al., "Thermodynamics of Dye Dimerization", *Chemical Physics Letters*, vol. 12, No. 2, pp. 259–260, Dec. 1971.

Lehninger, Biochemistry, Worth Publishers Inc, New York, NY, p. 873, 1976.*

* cited by examiner

NH-Gly-Ser-Gly-Ser-Arg-Leu-Pro-Gly-Pro-Ser-Asp-Thr-Cys n=2, 4, 6, 8
COMPOUNDS I, II, II, IV

COMPOUNDS V

COMPOUNDS VI

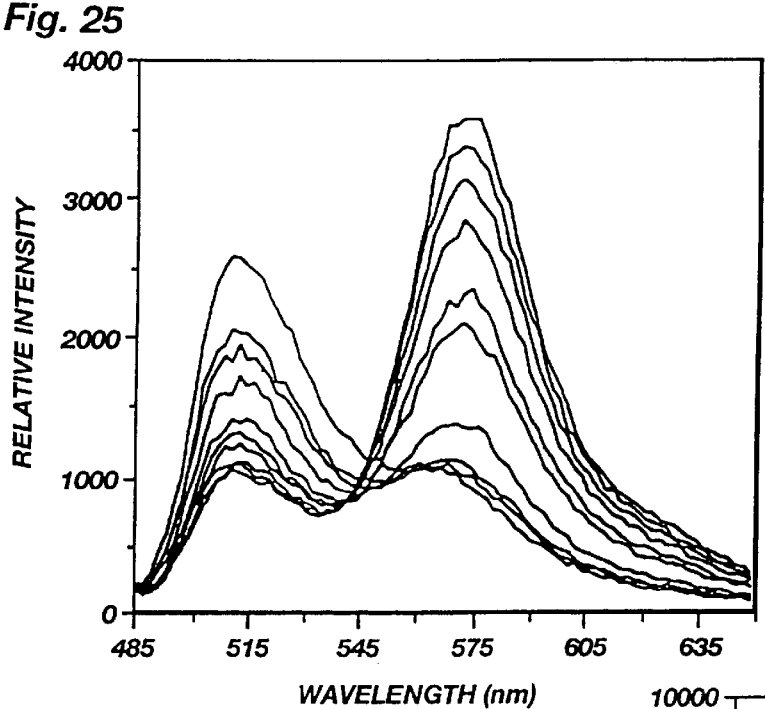
Fig. 25
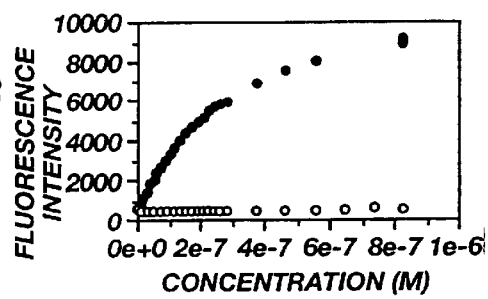
Fig. 26B
Fig. 26A
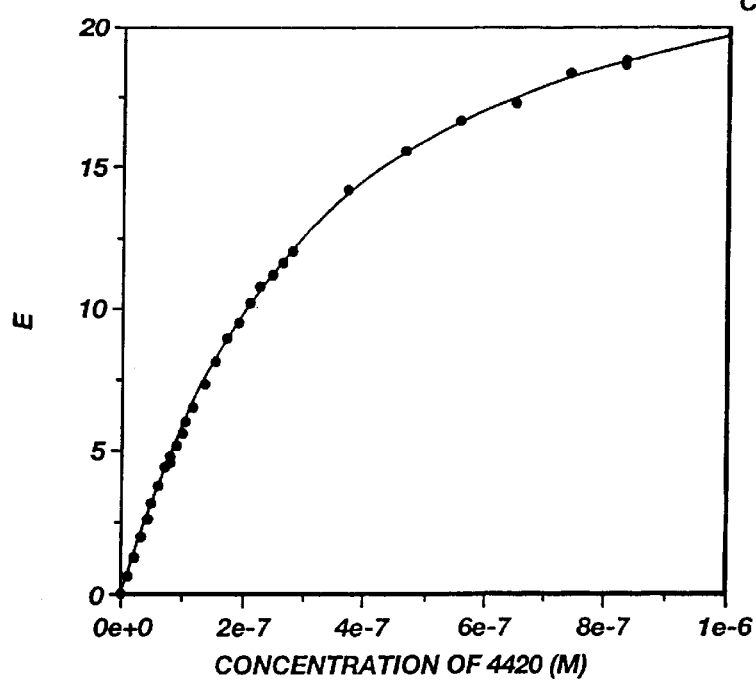

ASSAY PROCEDURE USING FLUOROGENIC TRACERS

RELATED APPLICATION

This application is a continuation of application Ser. No. 08/484,563, filed Jun. 7, 1995 now abandoned and a CIP of Ser. No. 08/096,338, filed Jul. 23, 1993.

TECHNICAL FIELD

This invention relates generally to biological assays, and more specifically to assay reagents labeled with fluorescent materials which reagents can be "toggled" from an intramolecular dimer to a fluorescent monomer by antibody binding.

STATE OF THE ART

Most clinical assays (e.g., immunoassays, DNA probe assays) are heterogeneous and consist of at least two steps: the binding of an antigen to its antibody, followed by physical separation of the bound from free antigens. In some more sensitive assays (e.g., "ELISA" or "EIA") multiple steps are required. Homogeneous immunoassays, on the other hand, can distinguish between bound antigens and free ones without the need of additional separation steps. They are simple, rapid, yet more precise, more cost effective, and have the potential for total automation. For these reasons, separation-free assays are preferred in many applications such as biosensors, bioprobes and other automated instrumentation. J. P. Gosling, Clin. Chem., 36:1408–1427 (1990), D. W. Chan and M. T. Perlstein, Eds., Immunoassay, A Practical Guide (Academic Press, New York, 1987), and E. F. Ullman and P. L. Khanna, Methods in Enzymology, 74:28–60 (1981).

However, because of various technical complications homogeneous systems have been difficult to obtain, with the exception of a few assays suitable only for small molecules. J. F. Burd et al., Clin. Chem., 23:1402–1408 (1977), M. E. Jolley et al., Clin. Chem., 27:1190–1197 (1981), and D. L. Morris et al., Anal. Chem., 53:658–665 (1981).

It would be an improvement in the art to develop and characterize new fluorogenic tracer antigens that can be used as "reporter molecules" for the binding event without the need of separation steps and the labeling of antibodies. The development of such tracers could greatly facilitate the automation of a large array of clinical assays, especially of high molecular weight antigens. It would help reduce the operational time and cost, and make such assays more readily accessible to doctors and patients. Also, such tracers would be extremely useful for rapidly screening large numbers of recombinant antibodies generated with genetic engineering techniques, such as those described in C. F. Barbas et al., Proc. Natl. Acad. Sci. USA 89:4457–4461 (1992), R. A. Lerner et al., Science 258:1313–1314 (1992), and Marks et al. J. Biol. Chem. 267:16007–16010 (1992).

DISCLOSURE OF THE INVENTION

The invention includes a fluorogenic tracer antigen that obviates the need for separation steps or the labeling of antibodies in the performance of an assay. The tracer is a short antigen-mimicking peptide labeled with both a fluorescent energy transfer donor and fluorescent energy transfer acceptor molecules. When free in solution, the tracer exhibits very low fluorescence due to intramolecular dye dimerization. After binding to an antibody of the native antigen, fluorescence is significantly enhanced as a result of the dissociation of intramolecular dimers brought about by conformational changes in the tracer peptide.

The invention thus includes an immunoassay procedure for detecting and quantifying unknown analyte antibody or analyte antigen in bulk solution, a reagent for use in such an immunoassay procedure, and a process for making such a reagent. The reagent which is used in the present procedure is a peptide epitope that is recognized by the antibody in bulk solution, the peptide epitope conjugated to a pair of fluorescent energy transfer dyes capable of moving between a stacked configuration to exhibit fluorescence quenching and a spaced (unstacked) configuration to exhibit fluorescence.

A procedure for using the previously described reagent in a homogeneous antibody assay includes: placing in bulk solution a conjugate of a peptide epitope for the unknown amount of analyte antibody, and a pair of fluorescent dyes. This reagent is capable of moving between a stacked configuration to exhibit fluorescent quenching and a more spaced configuration to exhibit fluorescence. Also placed into the bulk solution is the unknown antibody which will bind with the peptide epitope which is conjugated to the pair of dyes. When this binding event occurs, the configuration of the pair of dyes will be altered between an initial stacked configuration (when in solution) to an unstacked configuration, when the epitope is bonded to the antibody, with a concomitant increase in fluorescent energy in response to the binding.

It is also within the contemplation of the invention to design a homogenous antigen assay or a homogenous DNA (or RNA) probe assay.

The tracers have uses including homogenous detection of macromolecules (e.g. antibodies, antigens, DNA, and RNA) of clinical interest and rapid screening of recombinant antibodies.

BRIEF DESCRIPTION OF THE FIGURES

FIG. 25 is a graph depicting technical fluorescence spectra of F—$(CH_2)_6$—T (VI) ($3 \times 10^{-7}$ M) as aliquots of 4-4-20 solution were added. Ex=480 nm. The total 4-4-20 concentration varied from zero to $3 \times 10^{-7}$ M. In contrast to F—$(CH_2)_6$—T (III & V), the free F—$(CH_2)_6$—T (VI) conjugate has significant fluorescence from fluorescein and a shoulder peak due to rhodamine. Binding to 4-4-20, however, provides a flip-flop in the relative intensities of F and T.

FIG. 26 is a graph depicting fluorescence enhancement factor (E) at 589 nm as a function of 4-4-20 concentration ($P_o$). A solution of F—$(CH_2)_6$—T (VI) ($1.8 \times 10^{-7}$ M) was titrated with aliquots of stock 4-4-20 (filled circles, inset) and IgG+BSA (open circles, inset). Fluorescence intensity was measured at 589 nm with Ex=488 nm. A value of $5 \times 10^{-7}$ M was obtained for $K_d$.

BEST MODE OF THE INVENTION

Figure 1:
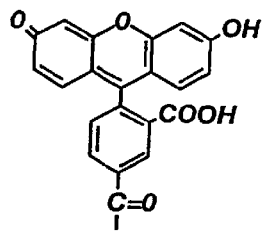
FIG. 1 depicts a doubly labeled oligopeptide useful in the practice of one embodiment of the invention.
Figure 1:
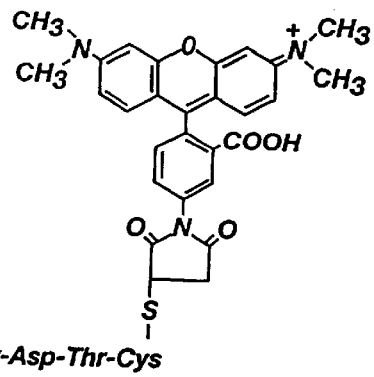

The "peptide epitope" used herein and to which the fluorescent dyes (preferably energy transfer dyes) are joined, either directly or through a spacer structure, is a relatively small, flexible peptide comprising alpha-amino acids which are joined together through peptide bonds. In general, there will be sufficient amino acids (e.g. from about 6 to about 13 amino acids) in the peptide to allow the peptide to fold upon itself. The term "epitope" is to be understood as relating to the specific surface of the native antigen (or "antigen") which is delineated by the area of interaction with an antibody of interest.

The peptide portion of the peptide epitope is an antigen or an antigen-mimicking peptide. Such a peptide may either be a sequential epitope which is a continuous sequence of the primary structure of the antigen; or an assembled epitope which consists of amino acids distant in the linear sequence, but brought together by tertiary structure folding. Several methods have recently emerged that enable rapid identification of high affinity binders for almost any monoclonal antibody. See, e.g. H. M. Geysen et al., Molecular Immunology 23:709–715 (1986), R. A. Houghten, et al., Nature 354, 84–86 (1991), K. S. Lam, et al., Nature 354:82–83 (1991) and J. K. Scott and G. P. Smith, Science 249:386–390 (1990).

The epitope may be chosen from any of various proteins where determining the presence of antibodies to the protein may be useful. These include epitopes from proteins associated with infectious diseases such as hepatitis B, hepatitis C, herpes simplex, and HIV. Epitopes from other useful proteins (such as rhesus factor) may also be used.

While not being bound by one theory of why the invention works so well, it is believed that antigen-mimicking peptides are more viable choices for the fluorogenic reporter molecules than their native antigens because of their small size. If a protein antigen is fluorescently-labeled, the changes in fluorescence signal (intensity, polarization, etc.) upon binding are relatively small. For this reason, previous homogeneous assays for high molecular weight antigens exhibited poor sensitivity. See, e.g. K. Nithipatikom and L. B. McGown, *Anal. Chem.*, 59:423–427 (1987). If fluorescently-labeled oligopeptides are used as tracers, however, significant changes in fluorescence signal upon binding occur presumably due to the oligopeptide's small size and chain flexibility.

The intended structure for the peptide epitope, in a preferred embodiment, can be determined by use of the epitope/mimotope screening techniques described in U.S. Pat. No. 4,833,092 to H. M. Geysen. In such a technique, a plurality of peptides having a defined linear sequence are synthesized, contacted with the antibody of interest, and the presence or absence of binding between peptide and antibody is determined. The presence of the highest level of binding identifies the preferred candidate or candidates for the peptide epitope for use in accordance with the present invention. Once the linear sequence of amino acids in the peptide epitope has been determined, it is well within the skill of persons in the art to synthesize such a peptide epitope using solid state peptide synthesis procedures. References which discuss the various synthesis methods available include: Merrifield, *J. Am. Chem. Soc.*, 85:2149–2154 (1963); M. Bodanszky et al., *Peptide Synthesis*, John Wiley & Sons, 2d Ed., (1976), and J. Stuart et al., *Solid Phase Peptide Synthesis*, (Pierce Chemical Company, Rockford, Ill., 3d Ed.), H. Neurath et al., Eds., pp. 104–237 (Academic Press, New York, N.Y. (1976)). Appropriate protective groups for use in such synthesis procedures are also known. See the above references as well as J. F. W. McOmie, *Protective Groups in Organic Chemistry*, (Plenum Press, New York, N.Y. (1973)).

For protein antigens of unknown primary sequence or other non-protein antigens, it is still possible to screen for high affinity binders to an antibody using Geysen's method or other more recent approaches based upon peptide libraries. See, e.g. the work of R. A. Houghten, et al., *Nature*, 354:84–86 (1991) and K. S. Lam, et al., *Nature*, 354:82–83 (1991).

Once obtained, the selected peptide epitope is then labeled with a pair of fluorescent energy transfer (namely, donor and acceptor) dyes which, when appropriately bonded to the peptide epitope to form a "conjugate", has the characteristic of dimerizing or "stacking" so as to quench any fluorescence of both fluorophores. The dye pairs do not necessarily have to be fluorescence energy transfer donor and acceptors. The type of dyes which do exhibit such stacking characteristics when bonded to the peptide epitope within a sufficiently close proximity to one another include those dyes which have a generally planar aromatic structure so as to be capable of forming homo- or heterodimers when in solution at concentrations which are sufficiently high for example, $10^{-3}$ to $10^{-4}$M).

It is well known that some fluorescent dyes (fluoresceins, rhodamines, cyanines, etc.) form dimers in aqueous solution when they are within close proximity of each other.

K. K. Rohatgi and G. S. Singhal, *J. Phys. Chem.*, 70:1695–1701 (1966); K. K. Rohatgi and A. K. Mukhopadhyay, *Chemical Physics Letters*, 12:259–260 (1971); and W. West and S. Pearce, *J. Phys. Chem.*, 69:1894–1903 (1965). Due to the interaction between transition dipoles of the resonating dimeric structure, these dimers exhibit very low fluorescence quantum yields. I. L. Arbeloa, *J. Chem. Soc. Faraday Trans.*, 2:1735–1742 (1981); I. L. Arbeloa, *J. Chem. Soc. Faraday Trans.*, 2 77:1725–1733 (1981); and I. L. Arbeloa and P. R. Ojeda, *Chemical Physics Letters*, 87:556–560 (1982). The monomers of these dyes, however, are highly fluorescent in aqueous solutions. For this reason, dye dimerization has largely been regarded as an adverse effect in biological applications. Bailey et al., *J. Pharm. & Biomed. Anal.*, 5:649–658 (1987). This invention uses this phenomenon to advantage. If two fluorescent dyes are conjugated to both ends of an antigen-mimicking peptide, it is probable that intramolecular dimers will form because of the planar structure of dyes and the short effective distance. This will result in significant fluorescence quenching. Upon binding to its antibody, however, the dye-peptide conjugate is expected to undergo conformational changes to accommodate to the active site. The fluorescence intensity will be enhanced as a result of dissociation of the intramolecular dimers.

Fluorescent energy transfer dyes of the fluorescein family, such as fluorescein, TMR, rhodamine B, and Texas Red are representative dyes of this type. Due to the interactions between the transition dipoles of the resonating dimeric structure, the fluorescent quantum yield of the dimer will be quite low when no antibody which can bind to the peptide epitope is present as compared to the significantly higher fluorescence quantum yield in aqueous solution when undimerized after the peptide epitope has become bound to the antibody. In this manner, a homogeneous antibody assay can be designed wherein labeled peptide epitope is placed in solution and the antibody analyte is added, so that the antibody and peptide bind, causing the dimerization to decrease with an attendant increase in fluorescence.

Fluorescein and TMR were used herein as the labels since, among other things, they are a well-characterized fluorescence energy transfer pair as well. Because this property may increase the Stoke's shift of the fluorescence emission, it is useful in reducing interference from scattering or serum fluorescence.

The invention is not limited to using fluorescent dyes. Organic ligands of some lanthanide metals, such as europium (Eu3+) and terbium (Tb3+) may also be used as labels. E. P. Diamandis, *Clin. Chem.*, 37:1486–1491 (1991). In the absence of antibodies, the peptide forms an intramolecular coordination complex with these ions. Such a complex is highly fluorescent and has fluorescence lifetimes ranging from $\mu$s to ms. If the peptide changes its conformation from a folded to a more extended state upon binding to its antibody, the coordination bonds with the metal could be broken, thus making the peptide non-fluorescent. Therefore, the fraction of bound and free tracers can be related to the net change in fluorescence intensities. Molecular dynamics and Monte Carlo simulations of the free peptide have shown that the distance between —SH and —NH2 groups is about 10 Å for the energy minimized conformational states. If coordination ligands, e.g., acetyl acetone or dipyridylamine, are introduced at these positions, they should fall within the coordination distance with Eu3+ or Tb3+. The extended length of a 13-mer peptide is about 50 Å which is far enough to break the coordination bond to release the ion, resulting in a dark species.

Solutions for use with the invention are ones in which the labeled peptide epitope and antibodies can be incorporated. They are generally buffered aqueous solutions and include buffered normal saline with a pH of 6 to 8.

A homogeneous antigen assay can also be designed wherein the aqueous solution contains antibodies and doubly labeled peptide epitope bound together so that the amount of intramolecular dimer formation is low thereby producing a high fluorescence signal. The addition of unlabeled analyte ligand, which binds to the antibody bonded to the peptide epitope, will result in a certain fraction of the doubly labeled peptide epitope being displaced from the antibody bringing about a concomitant decrease in fluorescence resulting from the formation of dimers in the labeled peptide epitope as it is displaced from the antibody.

Homogeneous assays can, therefore, be achieved by toggling the intramolecular monomer dimer equilibrium through the antibody-antigen binding event. For antibody assays, the sample is added to a solution of doubly-labeled peptide, and the net fluorescence increase is related to the antibody concentration.

For antigen assays, the sample is added to a solution of antibody mixed with the doubly-labeled tracer, and the net fluorescence decrease is related to the analyte concentration.

In analogy to the antibody-antigen system, this principle may also be utilized in DNA assays. If a DNA probe is used to link the two fluorophores, hybridizing with its target DNA will bring about a transition from intramolecular dimers to monomers. The target DNA can therefore be measured from the net increase in fluorescence intensity.

A homogenous DNA or RNA hybridization assay in which a pair of fluorophores (e.g. fluorescein and rhodamine, or Cy-3 and Cy-5) is attached to the 5' and 3' ends, respectively of an oligonucleotide (between 10 and about 30 nucleotides in length) which is complementary to a target DNA or RNA sequence that is part of a much larger piece of DNA (e.g. plasmid or chromosomal DNA) or RNA. The flourescently-labeled oligonucleotide would be mixed with the target DNA or RNA and the mixture heated to a temperature high enough to denature the double helix (alternatively, the target DNA could be denatured first, at which point the nucleotide could be added). As the mixture cools, the oligonucleotide would hybridize with its target sequence. The unbound form of the fluorescently labeled oligonucleotide would be non-fluorescent because of dimer formation between the two dyes. Upon hybridization however, this dimer would dissociate, resulting in an increase in fluorescence. As such, this is a homogenous, solution phase assay because no wash steps are required. Its sensitivity would be limited, however, by the sensitivity of the fluorometer for bulk fluorescence (e.g. one picomolar would be a practical limit with current instrumentation).

Greater sensitivity can be achieved by the use of a solid-phase evanescent assay. In this case, the fluorescently labeled oligonucleotide is attached to a waveguide via a non-stick layer (e.g. polyethylene glycol "PEG"), and the target DNA (or RNA) molecule is introduced to a sensor after being denatured (e.g. by heat). The assay would work in the same manner as the previously described homogenous DNA hybridization assay, but would have the advantage of the enhanced sensitivity associated with evanescent fluorescence. Potential detection limits would be 0.1 pM for a plastic waveguide sensor, and less than 1 femtomolar (fM) for IOW sensors.

Alternatively (to 10 to 30 base pair long DNA or RNA), longer nucleotide probes could be constructed by attaching the pair of fluorescent dyes to specially modified nucleotides in the middle of the probe, rather than at the 5'- and 3'-ends.

In the previously described DNA or RNA assays, nucleotide analogues that will hybridize with DNA and/or RNA, but are not degraded by plasma proteins may be advantageously substituted.

It is broadly within the scope of the present invention to immobilize the peptide epitope containing the pair of fluorescent energy transfer dyes which are capable of moving between stacked and unstacked configurations, on a waveguide through which light can be shown to generate an evanescent wave in the bulk solution. It is within this area of the evanescent wave that the fluorescent energy transfer characteristics of the selected dyes can be monitored to appropriately detect antigen-antibody binding events and thereby perform the immunoassay. However, a heterogeneous assay format is not the preferred embodiment. A homogeneous assay is preferred in view of simplicity and the absence of potential background signals due to the presence of the support as is well known to persons of ordinary skill in the art.

The fluorogenic tracer antigen described has many potential applications. First, its simplicity, speed, and sensitivity allow adaptation to existing automated instrumentation, such as the 96-well fluorescence plate reader or the TDX fluorescence polarization analyzer. Second, because labels all reside on the tracer peptide, fluorescent labeling of antibodies becomes unnecessary, thus eliminating the problem of reduced antibody activity often encountered. See, e.g. E. F. Ullman and P. L. Khanna, supra. Third, the doubly-labeled peptide has a very long Stroke's shift. If an argon ion laser (488 nm line) is used as the excitation source, the fluorescence emission can be measured at 576 nm, instead of 515 nm. The Stoke's shift of 90 nm helps to avoid interference from scattering and visible serum fluorescence at 500–515 nm. Fourth, since the fluorescein fluorescence (515 nm) remains constant after binding, it may be used as an internal self-reference point to correct for instrument fluctuations. Making use of this feature may also eliminate the need for standard curves in automated instruments. Fifth, in evanescent immunosensors, interference from bulk fluorescence is often a serious problem. See, e.g. V. Hlady et al., *Surface and Interfacial Aspects of Biomedical Polymers: Protein Adsorption*, J. D. Andrade, Ed. (Plenum Press, New York, 1985), pp. 81–119. If the doubly-labeled peptide is used as a tracer, it is fluorescent only when bound to immobilized antibodies and would become non-fluorescent when displaced into bulk solution, thus there should be no problem of bulk fluorescence. This would significantly reduce the stringency required for the optic detection system. Sixth, different fluorescent dye pairs may be labeled onto different tracer peptides, thus proving the possibility of detecting several analytes in the same sample simultaneously. Seventh, this concept may also be applied to the homogeneous detection of polynucleotides hybridization using a DNA probe labeled with two fluorophores.

The present invention is further illustrated with the following Examples:

EXAMPLE I

The hCG epitope peptide and its conjugate with dyes. A peptide from human chorionic gonadotrophin (hCG) was used as the spacer between fluorescein (F) and tetramethylrhodamine (T). Depicted in FIG. 1 is the structure of a hCG epitope peptide labeled with fluorescein and TMR. The peptide was identified by screening 221 (24) overlapping octapeptides synthesized on the tips of 96-pin solid supports as described in H. M. Geysen et al., *Molecular Immunology*, 23:709–715 (1986).

According to the Geysen method, a series of n-8 overlapping octapeptides were synthesized on the tips of 96-pin solid supports and tested for specific binding with anti-hCG using a ELISA procedure. where n is the number of amino acid residues in a sequence. A total number of 221 octapeptides was screened because hCG has two chains and a total number of 237 amino acid residues: R. B. Carlsen et al., *J. Biol. Chem.*, 248:6810–6827 (1973); R. Bellisario et al., *J. Biol. Chem.*, 248:6796–6809 (1973).

A core sequence of RLPGPSD (SEQ ID NO:1) showed strong reaction with the anti-hCG Mab. In order to conjugate dyes to the peptide without compromising its binding properties, the sequence GSGSRLPGPSDTC (SEQ ID NO:2) was synthesized using standard Fmoc methodology (J. M. Stewart and J. D. Young, Eds., *Solid Phase Peptide Synthesis* (Pierce, Rockford, Ill., 1984)) and purified on reversed phase HPLC to >95% purity. Its chemical identity was confirmed by Fab mass spectra and amino acid analysis. The peptide was first reacted with TMR maleimide in 50 mM, pH 6 phosphate buffer for 48 hours to make oligopeptide labeled with TMR ("pepT"). All chemically reactive dyes used were purchased from Molecular Probes, Eugene, Oreg. After purification on reversed phase FPLC (C-18 column, particle size 15 mm, Pharmacia LKB), pepT was reacted with fluorescein succimidyl esters in 50 mM borate buffer, pH 8.5 for overnight to make FpepT. The dye-peptide conjugate has the chemical structure of F-GSGSRLPGPSDTC-T (FpepT) and is shown in FIG. 1. A gradient of acetonitrile in water was used to purify these conjugates. In a typical elution, the acetonitrile content was increased from 15% to 30% over a period of 20 minutes, followed by an isocratic elution at 30% acetonitrile. All solvents contained 0.1% trifluoroacetic acid. The molecular weight of FpepT measured by Fab mass spectra was 209T which is 18 mass unit higher than the expected value of 2073.19. The hydrophilicity of the peptide plus the bulky fluorophores probably have caused entrapment of a bonded water molecule inside the conjugate.

Except for Cys, the linker peptide sequence corresponds to a portion of the naturally occurring sequence near the C-terminus of hCG b chain. This sequence, rather than the core peptide, was used because the latter exhibited little affinity to the anti-hCG Mab after fluorescein is attached at its N-terminus.

Comparison of the absorption spectra of FpepT, Fpep, and pepT showed that the major absorption peak of fluorescein blue-shifted by 2 nm, while that of rhodamine red-shifted by 9 nm. Also, the long wavelength peak of rhodamine had actually become hypochromic by a factor of 1.6.

There are normally two electronic transitions in the visible absorption region of fluoresceins and rhodamines: upper and lower energy levels. The absorption spectrum of a monomer consists of an intense band at the longer wavelength and a shoulder at the short wavelength. The formation of dimers provides a "flip-flop" of these relative peak intensities so that the shorter wavelength transition is more hyperchromic. The changes in these two excited levels of the dimer have significant consequences on its fluorescence spectra. The hypochromativity of the longer wavelength transition suggests a relatively long lifetime of the lower energy level. Due to radiation-less transitions from the upper to the lower excited level, most of the dimer molecules are in the lower state which exhibits weak fluorescence emission. Therefore, this radiation-less relaxation process substantially contributes to the low fluorescence quantum yield of the dimer.

Because of these changes, the absorption spectra of FpepT exhibited a poor fit to the simple sum of those of Fpep and pepT (FIG. 2), suggesting that ground-state static interactions exist between F and T. These static interactions have significant effect on the fluorescence quenching.

Figure 2B:
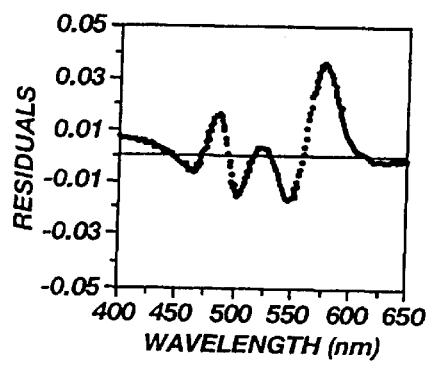
FIG. 2 is a graph depicting the absorption spectra of the FpepT conjugate (solid line).
Figure 2A:
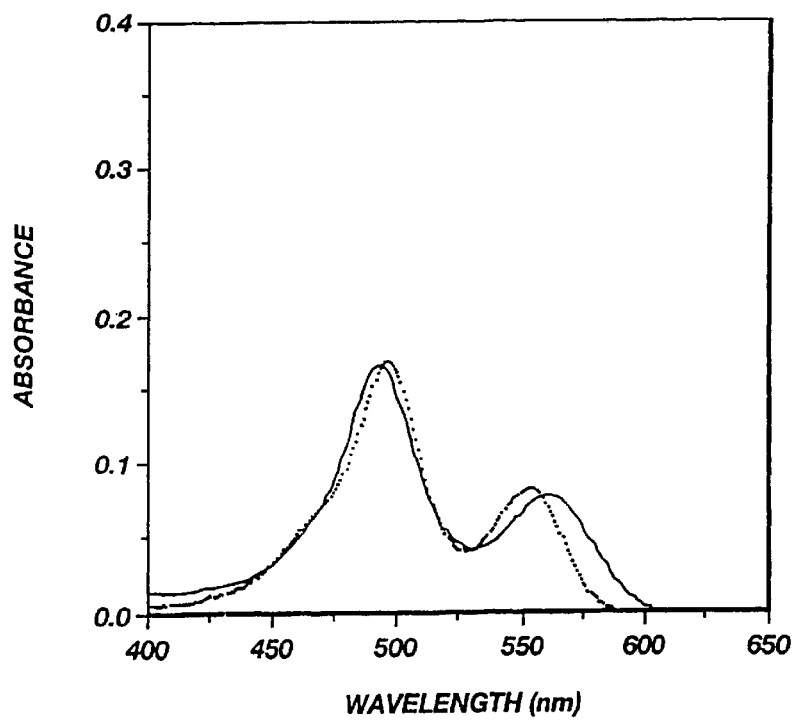

FIG. 2 graphically depicts the absorption spectra of the FpepT conjugate (solid line). The dashed line shows a least-squares fit of the spectra with a model assuming a simple mixture of Fpep and pepT according to the method of Wei, et al. *Biosensor Design and Application*, P. R. Mathewson and J. W. Finley, Eds. (American Chemical Society, Washington, D.C., 1992), vol. 511, pp. 105–120. The residual between the measured value and the fitted value at each wavelength is given in the inset. Because a perfect fit would generate a random residual plot with the average being zero, the systematic residual pattern in this figure indicates significant ground-state interactions between the two dyes in the same molecule. The concentration of this conjugate was deterrined by its absorbance at 560 nm using the molar extinction coefficient $$\epsilon_{560nm}^{1M}$$

of 60,000 $M^{-1}cm^{-1}$. The buffer system used for this spectra and an other subsequent fluorescent studies was 100 mM phosphate buffer, pH 7.4, unless otherwise stated.

Figure 3:
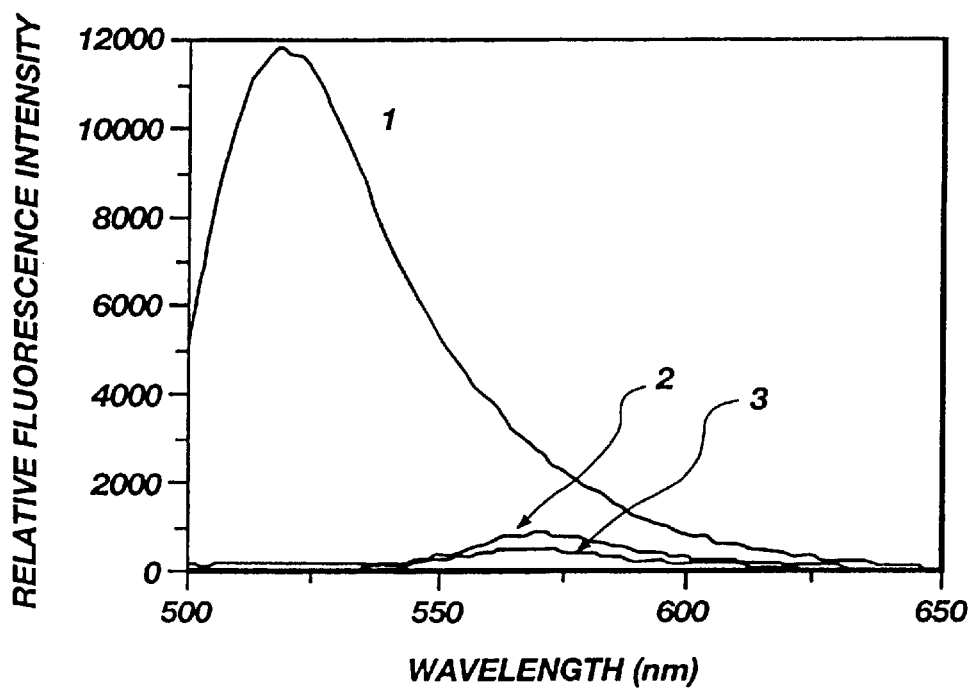
FIG. 3 is a graph depicting the relative fluorescence intensity vs. wavelength.

FIG. 3 depicts the technical fluorescence spectra of Fpep (1), pepT (2) and FpepT (3) when excited at 493 nm (c.a. $10^{-7}$ M). Compared to Fpep, the fluorescein fluorescence is quenched by 98% in FpepT.

Figure 4:
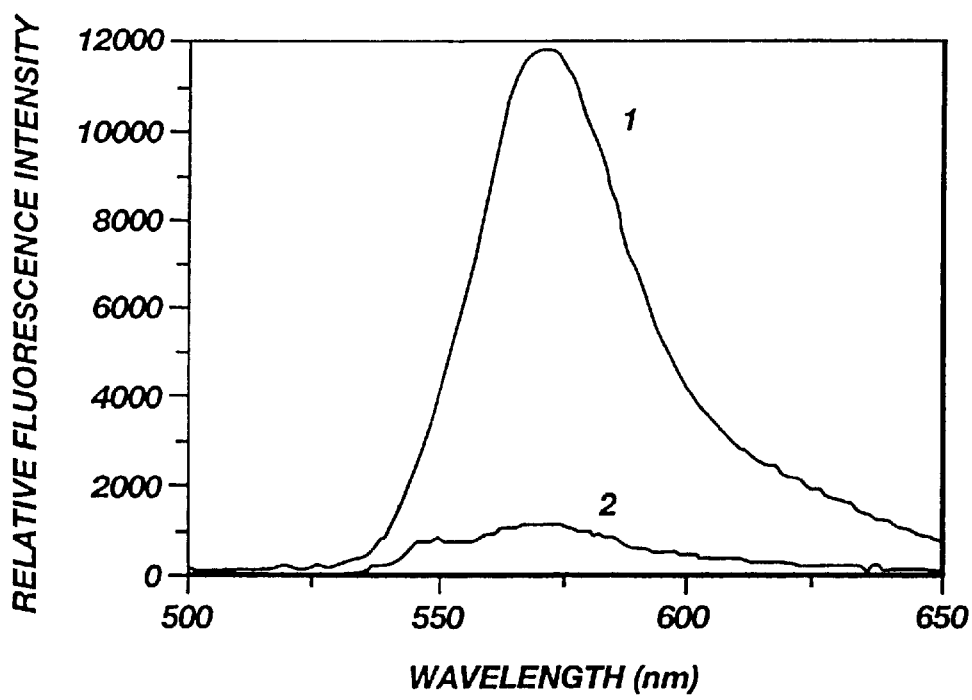
FIG. 4 is a graph depicting the relative fluorescence intensity vs. wavelength.

FIG. 4 depicts the technical fluorescence spectra of pepT (1) and FpepT (2) when excited at 550 nm ($10^{-7}$ M). Compared to pepT, the rhodamine fluorescence is quenched by 90% in FpepT. All fluorescence measurements (spectra, intensity, and polarization) were made with an ISS PC-1 fluorometer (ISS, Champaign, Ill.) at 6° C. unless otherwise indicated.

FIG. 3 shows that the intrinsic fluorescence of rhodamine in the FpepT conjugate is 10 fold lower than in the absence of F (i.e., 90% quenching) as a result of contacting with fluorescein. The fluorescein fluorescence of FpepT, on the other hand, is 64 fold lower than in the absence of T (i.e., 98% quenching). The higher quenching efficiency of the fluorescein fluorescence results from both the static interaction with and excited-stated energy transfer to rhodamine. These results strongly suggest that free FpepT indeed exists as intramolecular dimers.

EXAMPLE II

Binding of FpepT with anti-hCG Mab. The fluorescence spectra of FpepT upon binding to the anti-hCG Mab is presented in FIG. 5. The fluorescence of rhodamine (lambda max=570 nm) increased up to 5 fold with increasing antibody concentration as a result of diminished interactions with fluorescein. The fluorescein fluorescence (lambda max=515 nm), on the other hand, remained constant and quenched because of the fluorescence energy transfer from F to T. Since the distance at which 50% energy transfer efficiency occurs is 54 Å for the F-T pair, even if the peptide became fully extended after binding, the end-to-end distance of 47.19 Å would still allow 70% energy transfer efficiency. For this reason, the fluorescein fluorescence was not enhanced although the static quenching should be equally reduced for fluorescein as for rhodamine. The reduced ground state interaction between the two dyes can also be seen by comparing the absorption spectra of FpepT in the presence and absence of antibody.

Figure 6B:
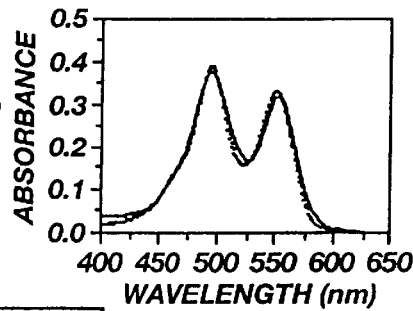
FIG. 6 is a comparison of the absorption spectra of FpepT ($6.5 \times 10^{-6}$ M) in the absence (dashed) and presence (solid) of anti-hCG antibodies ($7.5 \times 10^{-6}$ M).
Figure 6A:
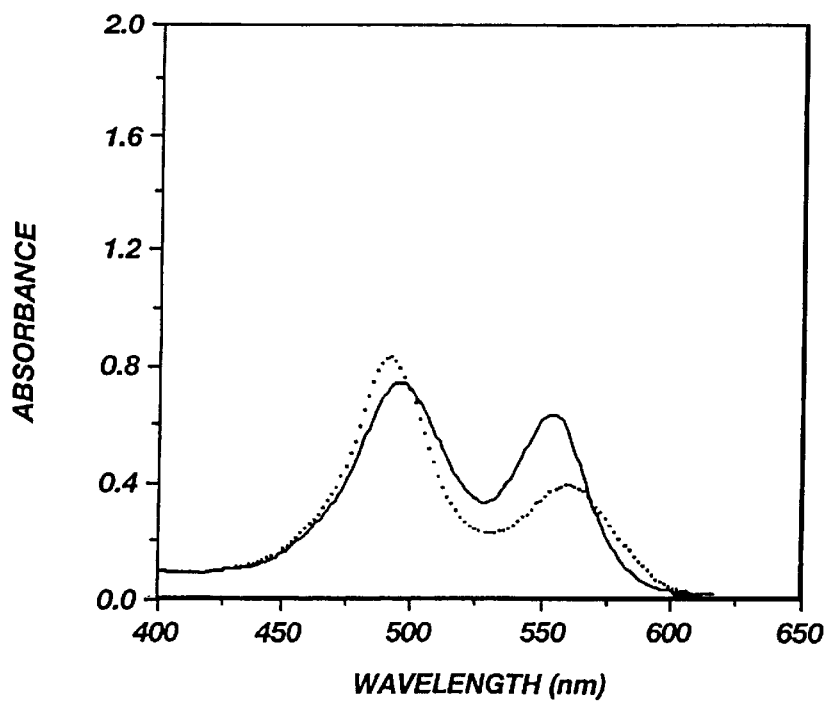

FIG. 6 compares the absorption spectra of FpepT (6.5× $10^{-6}$ M) in the absence (dashed) and presence (solid) of anti-hCG antibodies ($7.5 \times 10^{-6}$ M). After binding, the major absorption peaks of fluorescein and rhodamine have shifted more towards each other. As a result, the spectra can be better fitted with a model assuming a simple mixture of Fpep and pepT as shown in the inset. A.-P. Wei et al., in *Biosensor Design and Application*, P. R. Mathewson and J. W. Finley, Eds. (American Chemical Society, Washington, D.C., 1992), vol. 511, pp. 105–120. An anti-hCG monoclonal antibody from Organon Teknika, Boxtel, the Netherlands was used. It had been prepared according to the procedure of R. v. Erp et al., *J. Immunol. Methods*, 140:235–241 (1991). Antibody concentration was determined from its absorption at 278 nm, using an extinction coefficient of 14. Mouse immunoglobulin and bovine serum albumin were purchased from Sigma Chemical Co. (St. Louis, Mo.).

As shown in FIG. 6, the major absorption peaks of fluorescein and rhodamine have shifted toward each other after binding. And, the absorptivity of the rhodamine moiety has increased by a factor of 1.6 because of dimer dissociation. As a result, the spectra could be better approximated by a simple mixture of the two respective dyes (FIG. 6, inset), indicating that the bound form of FpepT has less spectral perturbation than the free species. It should be noted, however, that the measured spectra of the bound species do not completely coincide with the fitted spectra due to residual spectral perturbations that still exist.

Figure 7A:
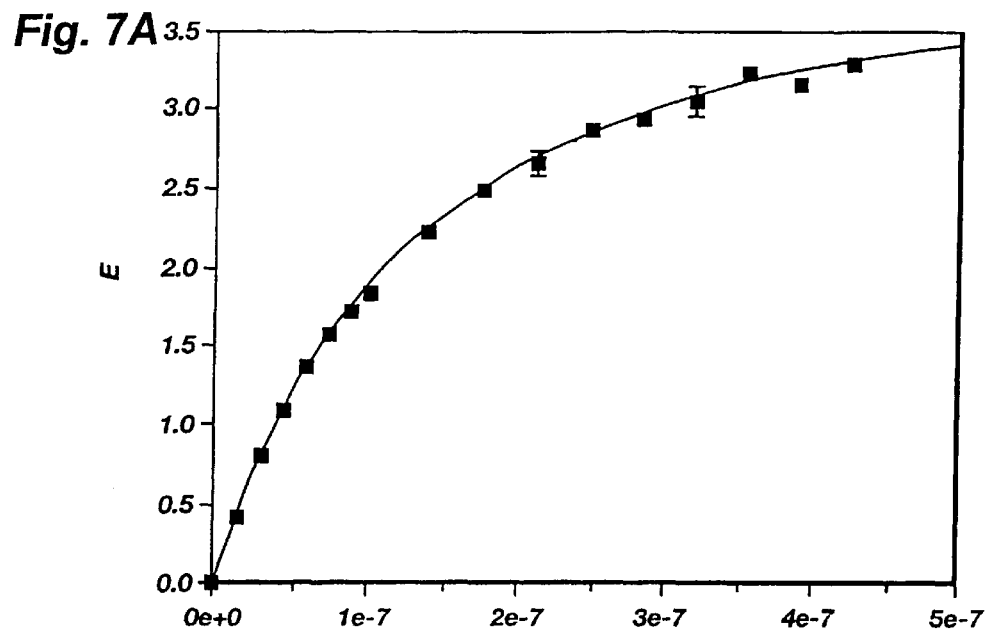
FIG. 7 depicts graphically the fluorescence enhancement factor E as a function of antibody concentration (EXX=493 mn and EM=590 nm).
Figure 7B:
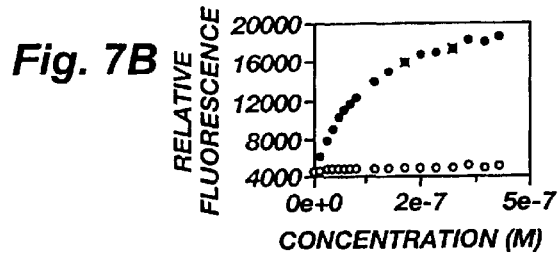

A typical intensity-versus-antibody concentration profile for the binding of FpepT with anti-hCG Mab is presented in FIG. 7. FIG. 7 depicts graphically the fluorescence enhancement factor E as a function of antibody concentration (EX=493 nm and EM=590 nm). Fluorescence intensities of FpepT ($1.3 \times 10^{-7}$ M) in sample (Is, filled circle) and reference (Ir, open circle) cuvettes as aliquots of stock anti-hCG and BSA & mouse IgG solutions were added are shown in the inset. The value of E was calculated from.

$$E = \frac{Is - Ir}{Ir}$$

The E~Po curve was fitted with the following equation using Kaleidagraph (Abelbeck Software):

$$2Po = \frac{KdE}{Em - E} + \frac{LoE}{Em}$$

where Po, Lo, Em and Kd are the total antibody concentration, total FpepT concentration, maximum enhancement, and dissociation constant, respectively. The values of Kd and Em were found to be Kd=$2.2 \times 10^{-7}$ M and Em=4.1, respectively. A higher value of Em (Em=6.8) was obtained for EX=561 nm and EM=590 nm.

While the addition of anti-hCG resulted in gradual increase in fluorescence, the same amount of bovine serum albumin and nonspecific mouse IgG did not have any effect on the fluorescence of FpepT, indicating that the enhanced fluorescence is a result of specific binding. The fluorescence enhancement factor (E) as a function of antibody concentration (Po) was fitted with a classical binding equation (FIG. 7, inset). The maximum enhancement (Em) at 590 nm was found to be 6.8 (ex=561), 4.1 (ex=493, data not shown), respectively. The dissociation constant (Kd) was ($2.2 \pm 0.3$)$\times 10^{-7}$ M (N=6). When the same peptide was studied in the absence of fluorescein (i. e. with only rhodamine at the Cys position), the value of Kd was found to be $0.67 \times 10^{-7}$ M. The three-fold decrease in binding affinity after labeling with fluorescein was probably caused by either steric hindrance or conformational differences between these two labeled forms of the peptide.

Compared to FIGS. 3 & 4, Em values of 4.1 and 6.8 should correspond to 51% and 78% of the intrinsic fluorescence of TMR, respectively. Results of control experiments confirmed this prediction. In a separate binding experiment, an antibody solution of fixed concentration was titrated with aliquots of FpepT. The curve of E vs. FpepT concentration (Lo) was fitted with a classical binding equation (FIG. 8).

Figure 8B:
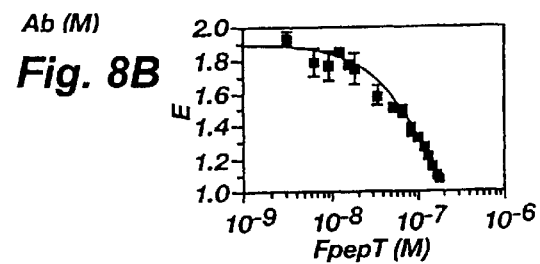
FIG. 8 graphically depicts the fluorescence intensities as a function of FpepT concentration (EX=561 nm and EM=590 nm).
Figure 8A:
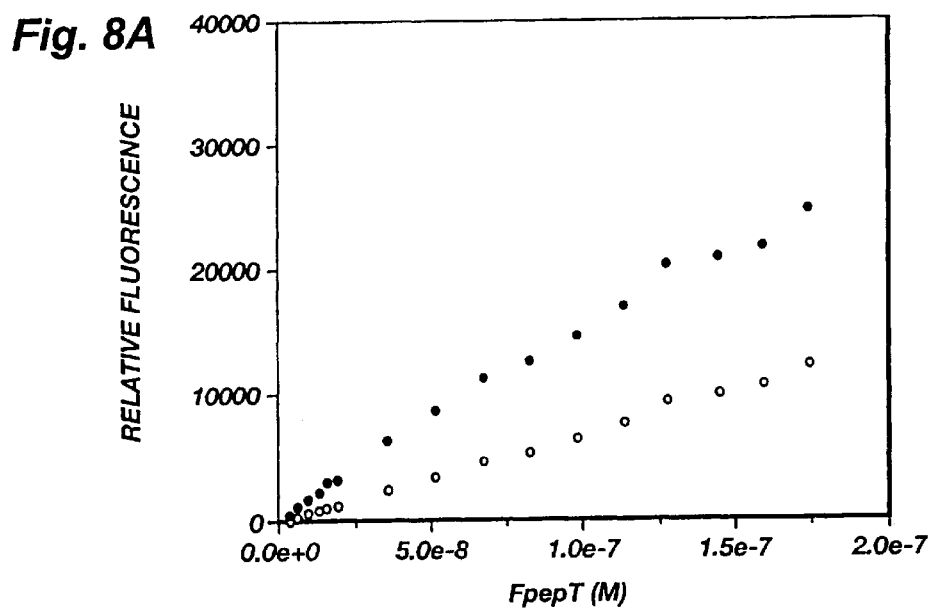

FIG. 8. graphically depicts the fluorescence intensities as a function of FpepT concentration (EX=561 nm and EM=590 nm). Sample cuvette contained $1.4 \times 10^{-7}$ M anti-hCG, and the reference cuvette contained $1.5 \times 10^{-5}$ M of BSA and mouse IgG. The Lo~E curve was fitted with the binding equation using Kaleidagraph (inset):

$$Lo = 2Po\frac{Em}{E} - \frac{KdEm}{Em - E}$$

The value of Kd was ($2.1 \pm 0.4$)$\times 10^{-7}$ M (N=3), in excellent agreement with the result of FIG. 7.

EXAMPLE III

Binding specificity and reversibility. Aliquots of hCG were added to a mixture of FpepT and anti-hCG to displace FpepT from the antibody. As the hCG concentration was increased, a series of spectra similar to FIG. 5 but in reverse order were obtained, indicating the bound fraction of FpepT was decreased (spectra not shown).

Figure 9A:
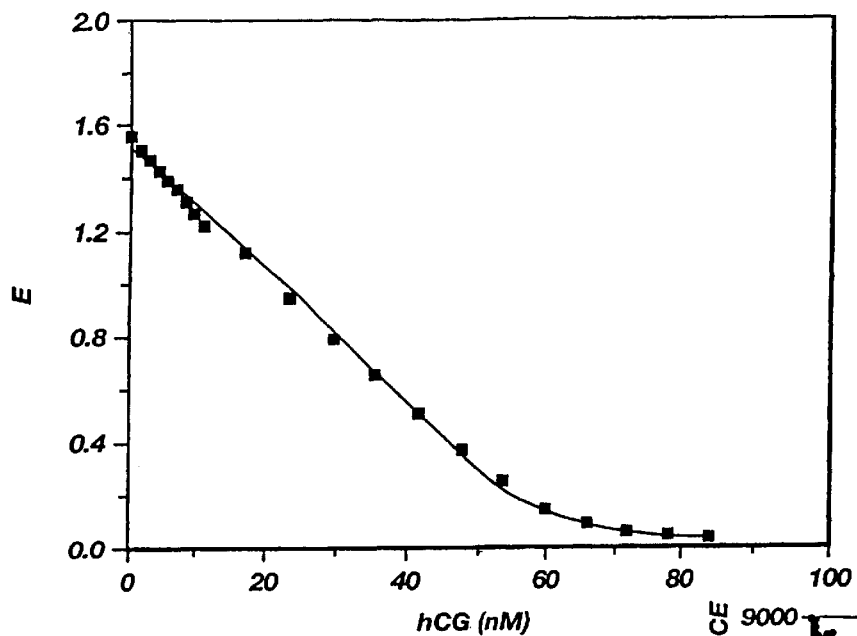
FIG. 9 graphically depicts the exchange of FpepT by hCG (EX=561 nm and EM=590 nm) in an antigen assay according to the invention.
Figure 9B:
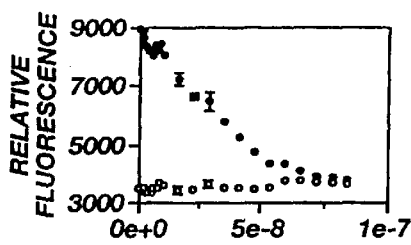

FIG. 9. graphically depicts the exchange of FpepT by hCG (EX=561 nm and EM=590 nm). A mixture of FpepT ($5.5 \times 10^{-8}$ M) and anti-hCG Mab ($4.5 \times 10^{-8}$ M) was first prepared, and 5 $\mu$l aliquots of hCG stock solution (1100 IU/ml) were added to the mixture. The reference cuvett contained only FpepT without antibody. The decrease in fluorescence intensity (inset) is due to displacement of FpepT by hCG. The fraction of bound FpepT (f2=E/Em) and the total hCG concentration (L°1) follows the equation:

$$L°1 = \left[\frac{K1(Em - E)}{K2E} + 1\right]\left[2Po - \frac{K2E}{Em - E} - (L°2)\frac{E}{Em}\right]$$

where K1, K2, Po, and (L°2) are the disassociation constants of hCG and PpepT, total antibody concentration, and total FpepT concentration, respectively. The data set of E vs. hCG(l°l) was fitted with the above model. The values of K1, K2 were found to be $4.9 \times 10^{-10}$ M and $2.4 \times 10^{-7}$ M, respectively. Human chorionic gonadotrophin (hCG) was a gift from Organon Teknika, Boxtel, the Netherlands. The concentration of hCG was converted from IU/ml to mole/l using a specific activity of 11,200 IU/mg for highly purified hCG and a molecular weight of 38,000.

FIG. 9 shows the fluorescence intensity as a function of concentrations of hCG, BSA & mouse IgG. The decrease in fluorescence at 590 nm is only specific to hCG, and little change was brought about by the non-specific proteins. These results confirmed the expectation that FpepT binds specifically to the same active site as hCG. The enhancement factor (E) vs. hCG concentration was fitted with a binding equation. The values of Kd for hCG and FpepT were found to be $4.9 \times 10^{-10}$ M and $2.4 \times 10^{-7}$ M, respectively. In spite of the 490-fold lower affinity exhibited by the tracer, the lowest detection limit of hCG was about $1 \times 10^{-9}$ M. This excellent assay performance is attributed to the fluorogenic properties which allow preferential measurements of the bound tracer.

EXAMPLE IV

Figure 10:
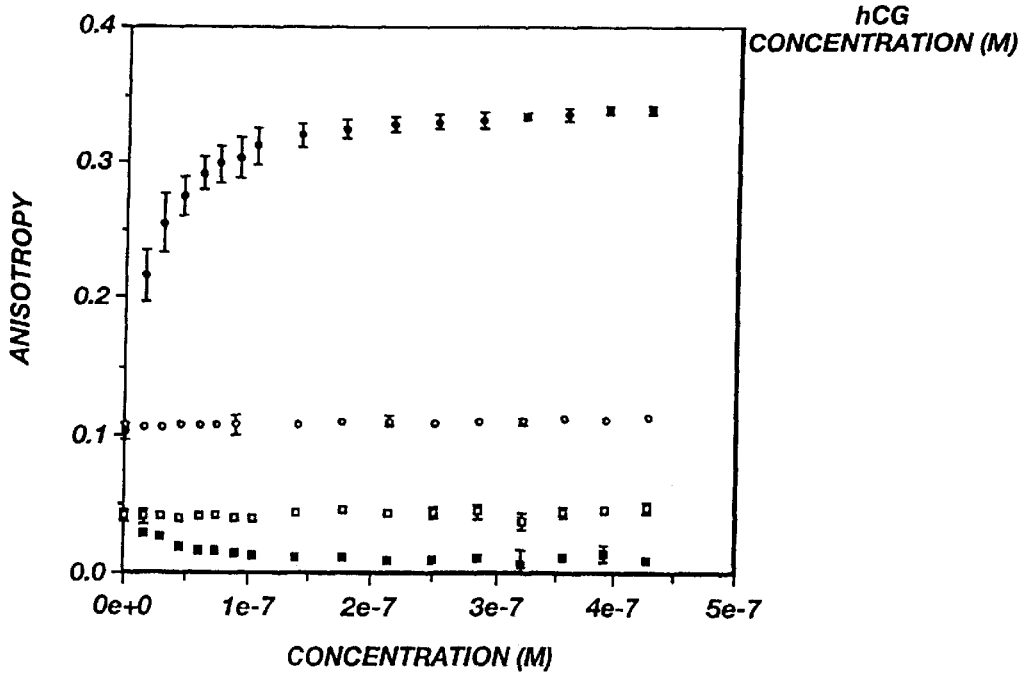
FIG. 10 is a graph depicting the fluorescence anisotropy of FpepT ($1.6 \times 10^{-8}$ M).

Fluorescence anisotropy. The anisotropy of rhodamine when excited at 550 nm as a function of anti-hCG concentration is shown in FIG. 10. In FIG. 7, (for excitation at 550 nm) anisotropies at 590 nm as a function of concentrations of anti-hCG and BSA & IgG are shown as filled and open circles, respectively. The error bars represent the standard deviations of three different experiments. The free FpepT has an anisotropy value of $A_f=0.1087\pm0.0014$ (N=17). The anisotropy value for bound FpepT is $A_b=0.3444$. Similar results were obtained for ex=490 nm and em=515 nm (not shown). For excitation at 490 nm, anisotropies at 590 nm as a function of concentrations of anti-hCG and BSA & IgG are shown as filled and open squares, respectively. This property can be used for a fluorescence polarization assay.

The more than 3-fold increase in anisotropy was attributed to the large difference in size between FpepT (MW=ca. 2000) and the antibody (MW=ca. 150,000). Similar result was obtained for the anisotropy of fluorescein when excited at 490 nm (data not shown). Because the emission was from the low-energy absorption band in these measurements, the limiting anisotropy value is expected to be in the range of 0.39–0.4 for both fluorophores. If the rotational diffusion of the intact IgG and the Fab fragments is taken into account, the observed maximum anisotropy value of 0.3444 for the bound FpepT suggests that both fluorophores have little rotational mobility in the antibody-FpepT complex, because of the small sized antibody active site and the bulky fluorophores.

When, however, the excitation was 490 nm and fluorescence was measured at the rhodamine emission, a completely different trend of change in anisotropy was obtained. Under this condition, because the high-energy absorption band was excited, the anisotropy is more a measure of the angle between the absorption and emission dipoles. The anisotropy of the free FpepT was $0.0436\pm0.0023$ (N=17), as compared to $0.1087\pm0.0014$ (N=17) when excited at 550 nm. The depolarization effect is caused by the noncolinearity between the absorption dipole at 490 nm and the emission dipole. As the anti-hCG concentration was increased, if there were no change in the angle between these two dipoles, an increase in anisotropy due to the diminished rotational motion would be expected. However, the data shows that increasing amount of antibody actually results in a gradual decrease in the anisotropy which saturates at near zero. This phenomenon strongly indicates that the angle between the two dipoles of FpepT had actually become larger when bound.

Figure 5:
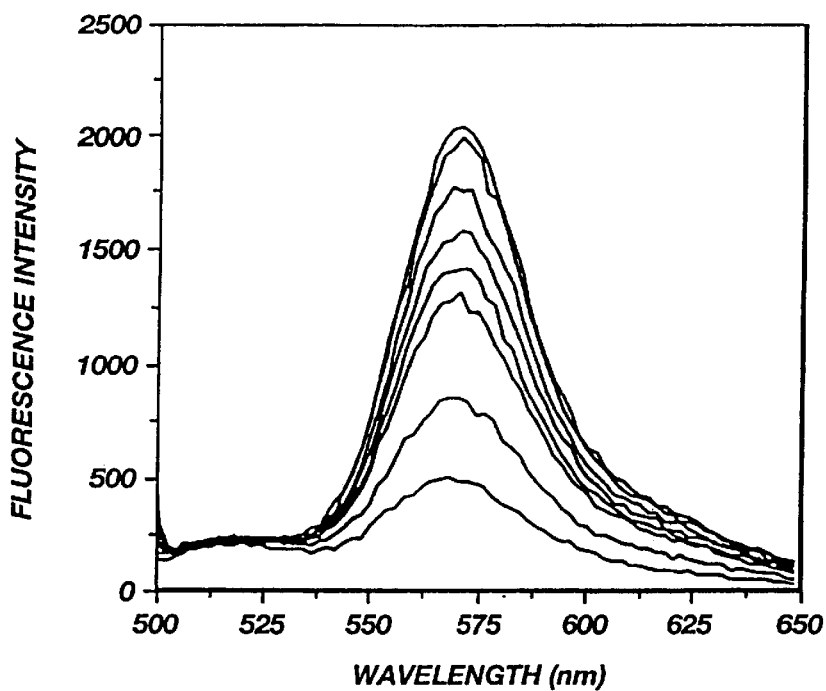
FIG. 5 graphically depicts the technical fluorescence spectra of FpepT ($10^{-7}$ M) as 5 $\mu$l aliquots of stock anti-hCG Mab were added. The total anti-hCG concentration changed from zero to $2.6 \times 10^{-7}$ M at an increment of $3.7 \times 10^{-8}$ M with a dilution factor of 2%.

These results, together with those depicted in FIGS. 5 and 6, support the conclusion that the observed fluorescence enhancement was indeed due to the dissociation of the intramolecular dimers between fluorescein and rhodamine as a result of conformational changes in FpepT.

EXAMPLE V

Figure 11:
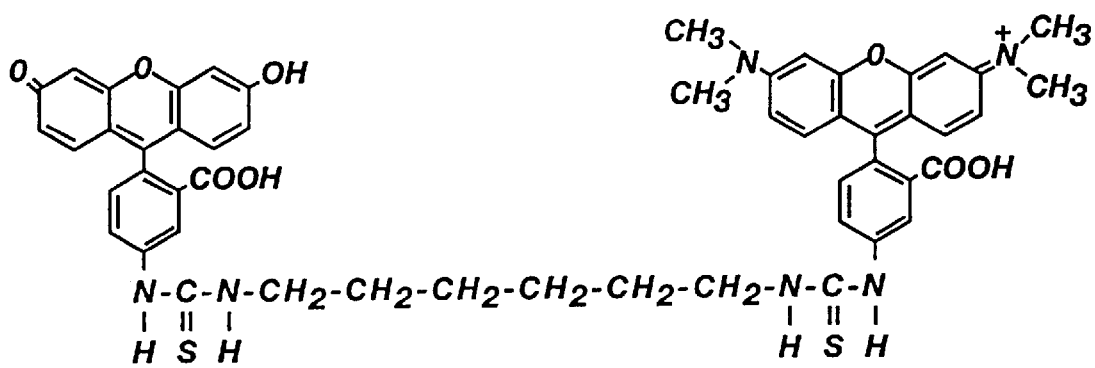
FIG. 11 depicts the chemical structure of a dimeric conjugate consisting of fluorescein and tetramethylrhodamine ("TMR") linked via a hexane spacer in a model system.
Figure 12:
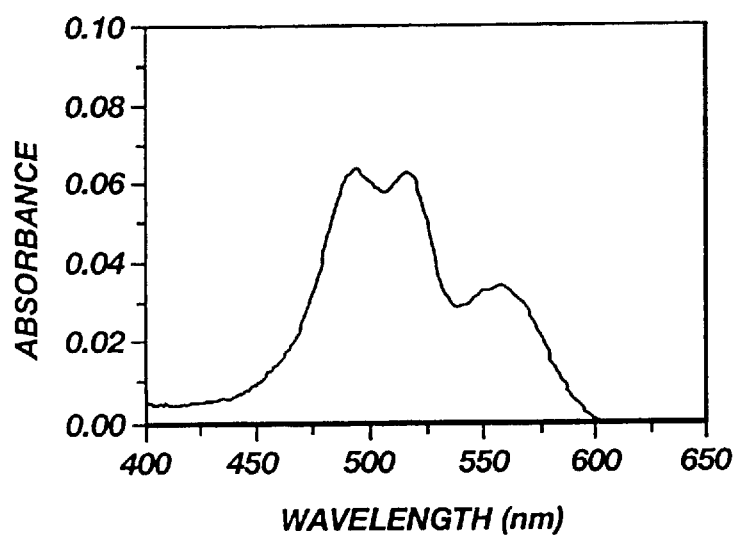
FIG. 12 is the absorption spectra of the conjugate shown in FIG. 11.

Fluorescein/anti-fluorescein as a model system. In addition to the hCG/anti-hCG system, a model system was also studied which consists of an anti-fluorescein Mab (4-4-20) and an antigen made of fluorescein linked to rhodamine via a hexane spacer (i.e. FhexT). The structure of this conjugate is shown in FIG. 11. To make FhexT, diaminohexane was reacted with an equal molar mixture of 5-isothiocynates of fluorescein and TMR in 100 mM carbonate buffer, pH 9.5 for overnight. The FhexT conjugate was isolated from the reaction mixture on reversed phase FPLC using the same condition as in FIG. 2. The absorption spectra of this conjugate is shown in FIG. 12. The bands at 515 mn and 555 nm are characteristic of the spectral splitting due to ring stacking as observed for rhodamine homo-dimers. I. L. Arbeloa and P. R. Ojeda, *Chemical Physics Letters* 87:556–560 (1982).

Figure 13:
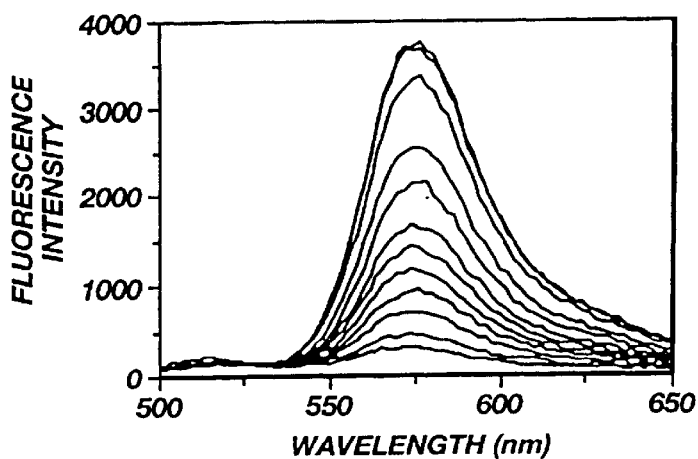
FIG. 13 depicts the technical fluorescence spectra of the FhexT conjugate ($4.35 \times 10^{-7}$ M) as aliquots of (Fab')2 fragment of antifluorescein 4-4-20 were added.

Concentrations of the conjugates used in FIG. 12 were determined from the absorbance at 556 nm using the extinction coefficient of 58,000 M-1 cm-1. In this particular case, however, the ring stacking is due to the formation of fluorescein-rhodamine hetero-dimers. Another indication of stacked dimer formation was the low level of fluorescence observed for FhexT. The fluorescence of free fluorescein or rhodarine at the same concentration would be about 1000-fold higher than that of the conjugate. As shown in FIG. 13, the fluorescence of rhodamine (lambda max=576 nm) increased with increasing concentrations of (Fab')2, an antigen-binding fragment of 4-4-20, while that of fluorescein (lambda max=515 nm) remains at a constant low level. This observation is consistent with the results of FIGS. 5 and 6, except that the enhancement in this case is about 400-fold, rather than 5-fold. This difference is attributed to two factors. First, the close distance between the two dyes in FhexT (~10 Å) allows almost 100% energy transfer efficiency from fluorescein to rhodamine. It also facilitates stacked dimer formation which quenches fluorescence more efficiently. Second, because fluorescein is the antigen in this system, it fits tightly into the binding site of the 4-4-20 Mab. J. N. Herron et al., *Proteins: Structure, Function, and Genetics,* 5:271–280 (1989). The static interaction with rhodamine after binding is thus diminished more effectively in this system than in the hCG/anti-hCG system. For these reasons, much higher enhancement of rhodamine fluorescence was observed. Binding specificity and reversibility of FhexT with 4-4-20 (Fab')2 was studied using 5-aminofluorescein are a nonfluorescent derivative of fluorescein. J. N. Herron, in *Fluorescein Hapten: An Immunological Probe*, J. E. W. Voss, Eds. (CRC Press, 1981) pp. 53–55.

The FhexT-antibody complex from the above titration experiments (FIG. 12) were titrated with 10 ml aliquots of 5-aminofluorescein (10–4M) in order to exchange the FhexT. Measurements were made after stirring for 2 minutes in the cuvette holder at 25° C. Spectra measured after 2 minutes and 30 minutes were found to be completely superimposable, indicating that binding equilibrium was achieved in a period of less than 2 min.

FIG. 13 is the technical fluorescence spectra of the FhexT conjugate ($4.35\times10^{-7}$ M) as aliquots of (Fab')2 fragment of antifluorescein 4-4-20 were added. The total (Fab')2 concentration changed from zero to $2.6\times10^{-7}$ M with a dilution factor of 3.6%. The concentration of (Fab')2 was determined by absorbance at 278 nm using an extinction coefficient of 1.5 and molecular weight of 110,000 daltons.

A series of spectra similar to FIG. 13 but in reverse order were obtained as increasing amount of aminofluorescein was added, resulting a typical exchange curve (data not shown). BSA was found to have no effect on the fluorescence intensity of FhexT in either bound or unbound state. These results indicate that the FhexT tracer binds to 4-4-20 specifically and reversibly. Although the PhexT/4-4-20 system needs to be further characterized to obtain biophysical parameters, it certainly serves as a template for optimizing the FpepT tracer or developing other tracers because of the efficient quenching and dramatic enhancement of fluorescence it exhibited.

Generality and fluorophore selection. The hCG/anti-hCG system described herein was completely a random choice.

From this stand-point, these results should be of general applicability. Although the hCG epitope was identified based upon the hCG sequence, recent peptide technologies have made it possible to identify a high affinity antigen-mimicking peptide for any monoclonal antibody. It therefore follows that the inventive approach may also be applied to protein antigens of unknown sequence or other non-protein antigens. Proper labeling of the peptide with fluorophores is the most critical aspect of these fluorogenic tracers. Although the core peptide is usually 6 to 8 amino residues in length, a longer sequence was used in order to reduce steric hindrance. The length of peptide will, in turn, determine what fluorophores to use. Assuming a typical dimerization constant of 2,500 M-1, the concentration of fluorescent dyes required to form 90% dimers is $1.8 \times 10^{-2}$ M which is $1 \times 10^{19}$ molecules/cm3. Under this condition, the average distance between two dye molecules is about 60 Å (measured from the centers of mass). Since the extended distance between alpha-carbons in polypeptide is 3.63 Å, the distance of 60 Å corresponds to about 16 amino acid residues. In other words, if the dye has a Kd of 2,500 M-1, the two fluorophores in the tracer can be spaced, at most, by 16 residues. This provides the basis for selecting fluorophores for a given peptide length. If the peptide is shorter than a 16-mer, fluorophores with smaller Kd should be used, and the vice versa, in order to achieve effective intramolecular dimerization. The dimerization constants of fluorescein, eosin, rhodamine B, rhodamine 6G are 5, 110, 2100, 5600 M-1, respectively (22, 33, 34), while that of cyanines varies in the range of 103–106 M-1 depending upon the chain length of the alkyl linkers in their structures. W. West and S. Pearce, *J. Phys. Chem.*, 69:1894–1903 (1965).

EXAMPLE VI

Materials and Methods
Chemicals and Reagents

The purified 5- and 6-isomers of fluorescein isothiocyanate and tetramethylrhodamine isothiocyanate, 5-(and-6) carboxyfluorescein succinimidyl ester, 5-(and-6) carboxytetramethylrhodamine succinimidyl ester were products of Molecular Probes (Eugene, Oreg.). Ethylenediamine, 1,4-butanediamine, 1,6-hexanediamine, 1,8-octanediamine, 5-aminofluorescein (isomer I) were purchased from Aldrich Chemical Company (Milwaukee, Wis.). All solutions were made in 100 mM phosphate buffer (pH 7.4) unless otherwise indicated.

Preparation of Antifluorescein Mab and Its Fragments

Antifluorescein monoclonal antibodies (Mabs) 4-4-20 and 9-40 were generated through chemically mediated fusion of BALB/c splenic lymphocytes with the Sp 2/0-Ag 14 myeloma cell line. Hybridoma cell lines were obtained from Prof. E. W. Voss, Jr. at University of Illinois at Urbana-Champaign. Kranz et al. *Mol. Immunol.*, 18:889–898 (1981); Bates et al. *Mol. Immunol.*, 22:871–877 (1985). Mabs were purified from mouse ascites fluid. Ammonium sulfate precipitation was followed by DEAE-cellulose anion exchange and chromatofocusing FPLC (Pharmacia) over a pH gradient of 7.0 to 5.0. Preparations were characterized by gel electrophoresis and fluorescence quenching assays. Herron, J. N. In *Fluoroscein Hupten: An Immunological Probe*, E. Voss Jr. Ed. (1981 CRC Press, Boca Raton, Fla.) pp. 53–55. Antibody solutions were filtered through Durapore 0.2 µm filters (Mipore, Bedford, Mass.) before use. The molar concentration of (Fab')$_2$ and intact antibody was determined by absorbance at 278 nm using an extinction coefficient ($\epsilon_{1cm}^{1\%}$) of 14 and molecular weight of 110 and 150 kDa, respectively, Preparation of F—(CH$_2$)$_n$—T Bichromophores Single-labeled conjugates were first prepared by reacting fluorescein-5-isothiocyanate (~5 mg) with ca. a 10-fold molar excess of either 1,2-ethylenediamine, 1,4-butanediamine, 1,6-hexanedianine, or 1,8-octanediamine in 100 mM carbonate buffer (pH 9.5) overnight at room temperature. The single labeled conjugates (F—(CH$_2$)$_n$—NH$_2$) were separated from reactants and other products using reversed phase FPLC (C-18 column, particle size 15 µm, Pharmacia LKB). Each reaction mixture was eluted at a flow rate of 1 ml/min with a linear gradient of deionized water (H$_2$O) and acetonitrile (ACN) both of which contain 0.1% trifluoroacetic acid (TFEA). For a typical elution, ACN was increased from 15% to 50% in a 45-minute interval followed by a 15-min isocratic elution at 50% ACN. In the second step, purified fractions of F—(CH$_2$)$_n$—NH$_2$ were reacted with excess tetramethyfrhodamme-5-isothiocyanate (~1.5-fold), respectively to make bichromophores. The reaction and purification conditions were the same as in the first step. In order to ensure purity, each of the F—(CH$_2$)$_2$—T, F—(CH$_2$)$_4$—T, F—(CH$_2$)$_6$—T, F—(CH$_2$)$_8$—T preparations were repurified using 50 mM phosphate buffer (pH 7.4), instead of deionized water, as the aqueous phase during the elution gradient. The chemical identity of these compounds was confirmed by fast atom bombardment (FAB) or electrospray (ES) mass spectrometry. The concentration of these bichromophores were determined from the rhodamine absorption maxima at ~560 nm using an extinction coefficient of 37,500 M$^{-1}$ cm$^1$. Similar reaction and separation conditions were used to prepare F—(CH$_2$)$_6$—T conjugates involving 6-isomers and amide linkages.

Spectral Analysis

Visible absorption spectra of F—(CH$_2$)$_n$—T in the absence and presence of 4-4-20 were subjected to multiple linear regression analysis using the model:

$$A_{F—(CH2)n—T} = \alpha \cdot A_{F—(CH2)6} + \beta \cdot A_{T—(CH2)5} + \epsilon \quad (1)$$

where $A_{F—(CH2)6}$, $A_{T—(CH2)5}$, and $A_{F—(CH2)n—T}$ are the absorption spectra (400–650 nm) of single-labeled and double-labeled conjugates, respectively; $\alpha$ and $\beta$ are linear coefficients to be determined; and $\epsilon$ is the residual term. The analysis was performed on an Apple Macintosh computer using StatWorks (Cricket Software Inc., Philadelphia, Pa.). All absorption spectra were measured on a Perkin-Elmer Lambda 2 UV/Vis spectrometer at room temperature (~25° C.)

Fluorescence Measurements

Fluorescence spectra, intensity, and anisotropy measurements were taken with an ISS PC-1 fluorometer (ISS, Champaign, Ill.). An excitation wavelength of 488 (fwhm dispersion=4 nm) was used, and fluorescence emission was measured through a 589 nm interference filter (fwhm=10 nm, Oriel, Conn.) superimposed with a 570 nm long pass filter (Schott, Pa.). Temperature was controlled at 25° C. using a water bath. In all titration experiments, the overall titrating volume added to the sample was less than 4% of the total sample volume.

Binding Experiments and Data Analysis

For each conjugate, two identical solutions of F—(CH$_2$)$_n$—T (~1×10$^{-8}$ M) were prepared. One was titrated with 5 µL aliquots of a stock 4-4-20 solution (sample), and the other with a 1:1 mixture of BSA and mouse IgG (reference). Fluorescence intensities in sample and reference cuvettes were denoted as $I_s$ and $I_r$, respectively. The background intensity ($I_b$) was measured before any conjugate and antibody were added. The enhancement factor is defined as:

$$E = \frac{I_s - I_r}{I_r - I_b} \quad (2)$$

Because these conjugates are nearly non-fluorescent (when not bound), the denominator term ($I_r-I_b$) is often very small. Any small variation in it could cause large changes in the value of E. In order to avoid this problem, we adopted a different form of this equation as shown below:

$$E = \left(\frac{I_s - I_r}{I_r}\right)\left(\frac{I_r}{I_r - I_b}\right) \quad (3)$$

Mathematically, this expression is equivalent to eq 2. It can be shown that E and the total antibody concentration ($P_o$) are related as follows:

$$2P_o = \frac{K_d E}{E_m - E} + \frac{L_o E}{E_m}, \quad (4)$$

where $P_o$, $L_o$, $E_m$ and $K_d$ are the total antibody concentration, total F—$(CH_2)_n$—T concentration, maximum enhancement, and dissociation constant, respectively. The E vs $P_o$ data set was fit to this equation using Kaleidagraph (Abelbeck Software). This procedure of determining binding parameters is referred to as method I in subsequent discussions. In an alternate method (method II), a sample solution of 4-4-20 ($1\times10^{-8}$ M) was titrated with 5 μL aliquots of stock F—$(CH_2)_n$—T. The same amount of F—$(CH_2)_n$—T was also added to a reference buffer solution. The relationship between total F—$(CH_2)_n$—T concentration ($L_o$) and E is given by the equation:

$$L_o = 2P_o \frac{E_m}{E} - \frac{K_d E_m}{E_m - E}, \quad (5)$$

where the parameters are defined the same as in eq 3. The E vs $L_o$ data set was fit to this equation using Kaleidagraph. Eqs 4–5 were derived from the basic mass law of binding equilibrium. Readers should refer to Herron (1981) supra or Pesce et al. for general derivation procedures. Pesce et al. *Flourescence Spectroscopy: An Introduction for Biology and Medicine* (Marcel Dekker NY 1971).

Results and Discussion

The Bichromophoric Conjugates

Figure 16:
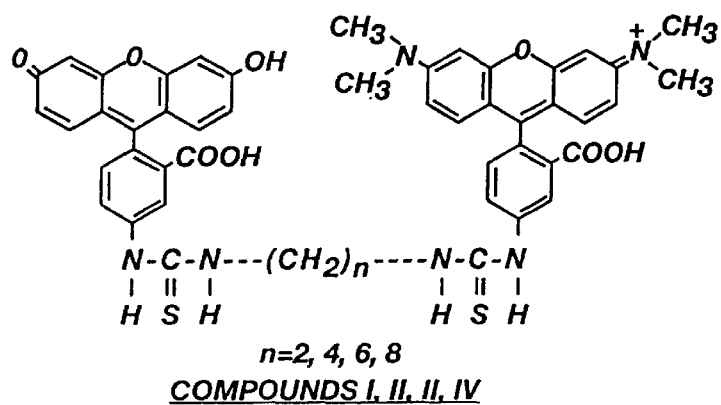
FIG. 16 depicts chemical structures of six bichromophoric conjugates consisting of fluorescein and tetramethylrhodamine linked by varying number of $CH_2$ units using different chemistry or isomers.
Figure 16:
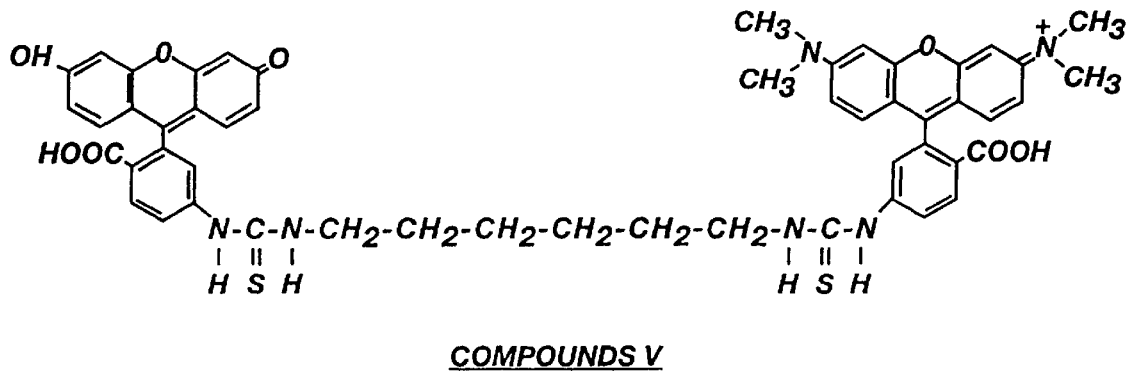
Figure 16:
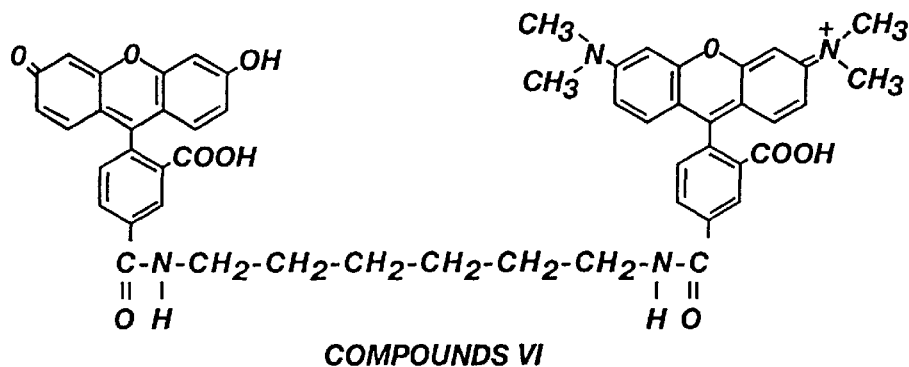
Figure 16:
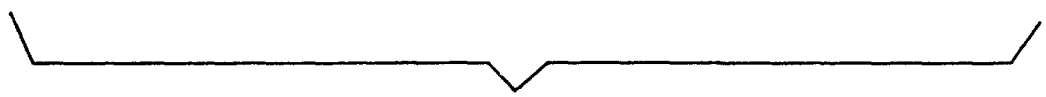

Six bichromophoric conjugates were studied. Their structures are shown in FIG. 16. They consist of fluorescein (F) linked to tetramethylrhodamine (T) by varying numbers of $CH_2$ units through thiourea bonds or amide bonds. A conjugate using the 6-isomers of F and T was also studied for the effect of isomeric states. These compounds were purified to >98% purity on reversed phased FPLC and stored at −20° C. Their chemical identity was confirmed by mass spectrometry the results of which are shown in Table 1. Because the thiourea bonds are relatively labile, chemical decomposition is possible after long-time storage, resulting in substantial increase in background fluorescence. In order to avoid this problem, conjugates were usually measured within three days of fresh preparation. If storage was beyond three days, they were repurified on an FPLC column before use.

Figure 17A:
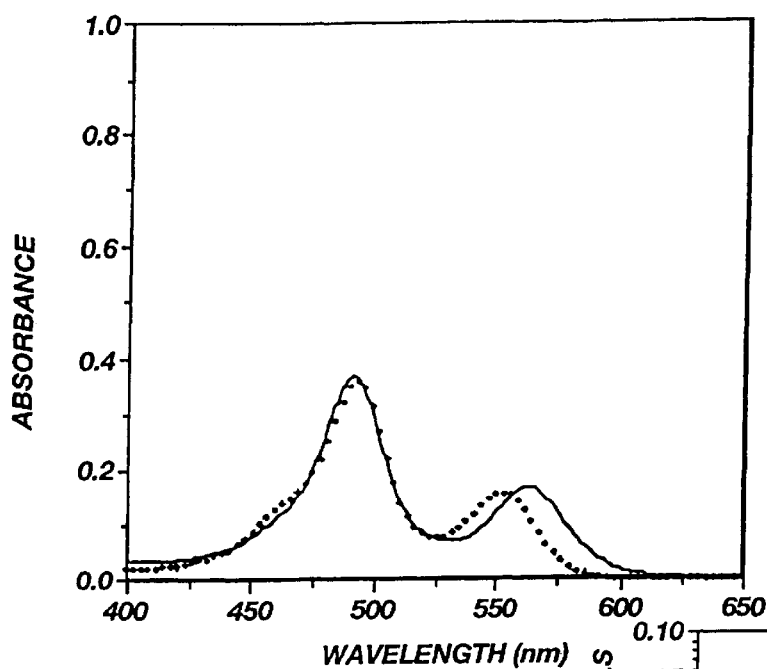
FIG. 17 depicts absorption spectrum of F—$(CH_2)_6$—T (III) (solid line). The dashed line shows a multiple linear regression fit of the measured spectrum to a model assuming simple summation of single-labeled conjugates. Discrepancies between these two curves (poor fit) indicate significant ground-state interactions exist between F and T in the conjugate. Similar results were obtained for conjugates I, II, IV, VI (data not shown).
Figure 17B:
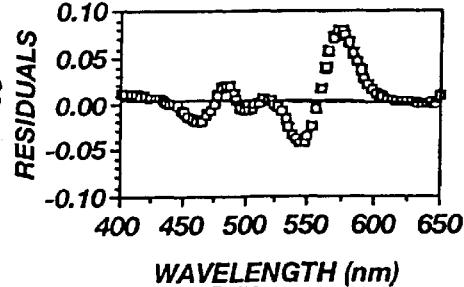

The F—$(CH_2)_n$—T conjugates were first examined for ground-state interactions between F and T. As an example, the absorption spectrum of F—$(CH_2)_6$—T (III) is shown in FIG. 17. It has two major electronic transitions in the visible region—491 and 563 nm—representing dipoles of fluorescein and tetramethylrhodamine, respectively. This spectrum was fit to eq 1 by a multiple linear regression procedure. Compared to the summed spectra of single-labeled conjugates, the absorption maximum of fluorescein is blue-shifted by 2 nm, while that of rhodamine is red-shifted by 11 nm. Similar results were also obtained for compounds with n=2, 4, 8 (data not shown), indicating that significant ground state interactions indeed exist between F and T in these conjugates.

TABLE 1

Description of six compounds shown in FIG. 16

| Compound | I | II | III | IV | V | VI |
|---|---|---|---|---|---|---|
| Linker Length | n = 2 | n = 4 | n = 6 | n = 8 | n = 6 | n = 6 |
| Chemistry | thiourea | thiourea | thiourea | thiourea | thiourea | amide |
| Isomeric State | 5, 5 | 5, 5 | 5, 5 | 5, 5 | 6, 6 | 5, 5 |
| Mol. Mass (C) | 893.00 | 921.05 | 949.11 | 977.16 | 949.11 | 886.96 |
| Mol. Mass (M) | 892.84 | 920.84 | 948.84 | 976.84 | 948.84 | 886 |

C - Calculated mass;
M - Measured by FAB or Electrospray mass spectrometry.

Figure 18:
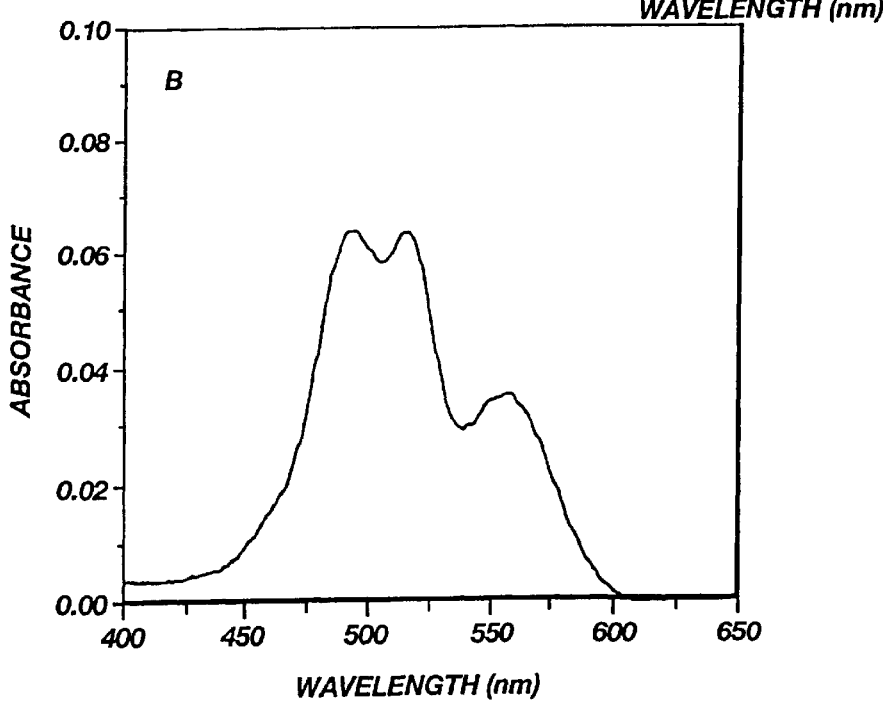
FIG. 18 is a graph depicting absorption spectrum of F—$(CH_2)_6$—T (V) which uses the 6-isomers of F and T, demonstrating intramolecular dimerization. The bands at 515 nm and 555 nm are characteristic of the spectral splitting due to ring stacking as often observed for rhodamine homo-dimers. In this particular case, however, the ring stacking is believed to be due to the formation of fluorescein-rhodamine hetero-dimers, instead of homo-dimers.

A more dramatic change in absorption spectra was observed for F—$(CH_2)_6$—T (V) which contains 6-isomers of F and T. As shown in FIG. 18, the absorbance consists of three separate transitions. The peak at 490 nm is attributed to fluorescein. Peaks at 515 nm and 555 nm are attributed to rhodamine in hetero-dimeric states with fluorescein. Normally, the absorption of rhodamine molecules consists of a major transition at 550 nm and a shoulder at about 30 nm to the blue. In monomeric states, the longer wavelength transition is the stronger of the two. However, dimerization provides a "flip-flop" of these relative peak intensities so that the shorter wavelength transition is more hyperchromic. The existence of these two excited levels of the dimer has significant consequences on its fluorescence quantum yield. The hypochromativity of the longer wavelength transition suggests weak oscillator strength and a relatively long lifetime of the lower energy level. Due to radiationless transitions from the upper to the lower excited level of the dimer, most of the dimer molecules may be in the lower state which exhibits weak fluorescence emission. Therefore, this radiationless relaxation process may substantially contribute to the low fluorescence quantum yield of the dimer. For this reason, these conjugates are nearly non-fluorescent (>99% quenching).

Binding of F—$(CH_2)_6$—T (V) with Antifluorescein 4-4-20

Figure 19:
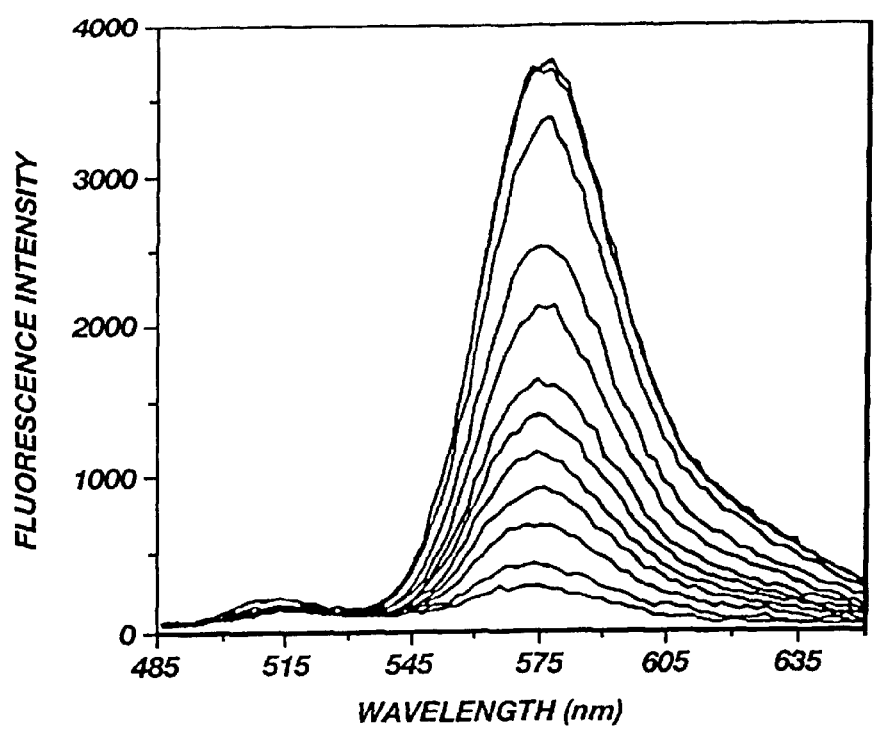
FIG. 19 is a graph depicting technical fluorescence spectra of F—$(CH_2)_6$—T (V) ($4.35 \times 10^{-7}$ M) as aliquots of (Fab')$_2$ fragment of antifluorescein 4-4-20 were added. Ex=475 nm. The total (Fab')$_2$ concentration varied from zero to $2.6 \times 10^{-7}$ M. Measurements were made in 100 mM phosphate buffer, pH 7.4 at 25° C. After each addition of (Fab')$_2$ aliquots, samples were stirred for 2 min before measurements were taken to allow for equilibration. The overall titrating volume was less than 4% of the total sample volume.
Figure 23:
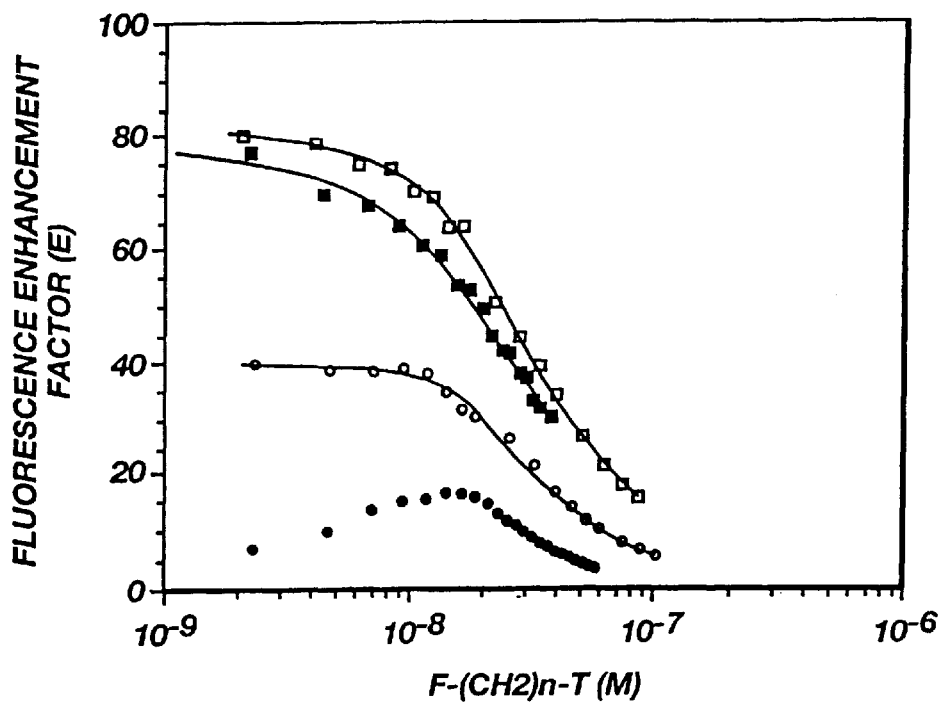
FIG. 23 is a graph depicting fluorescence enhancement factor (E) at 589 nm as a function of concentration ($L_o$) of conjugates I (n=2, filled squares), II (n=4, open squares), III (n=6, open circles) and IV (n=8, filled circles).
Figure 24:
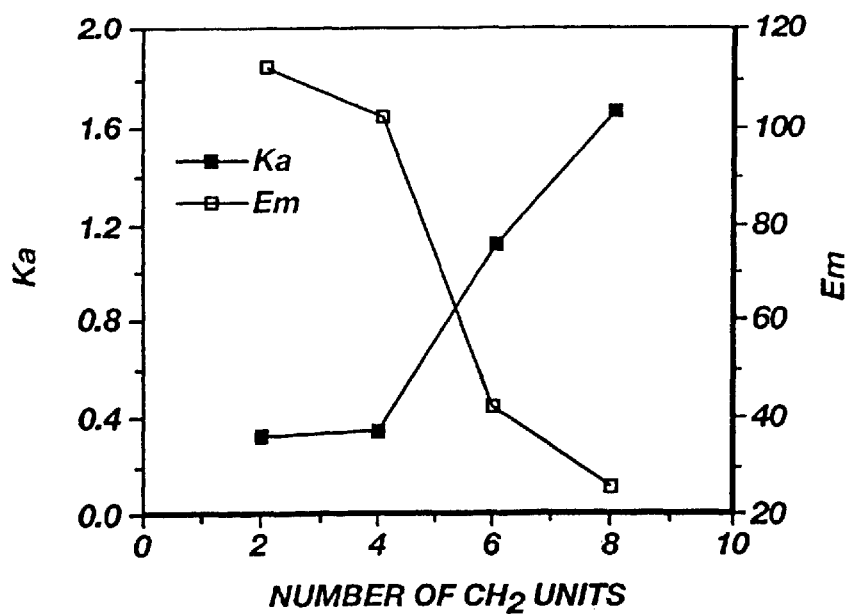
FIG. 24 is a double-axis plot of $K_a$ and $E_m$ as a function of number of $CH_2$ units in linker according to results obtained from FIG. 20.

As shown in FIG. 19, the fluorescence of F—$(CH_2)_6$—T increased with the concentration of (Fab')$_2$—a bivalent antigen-binding fragment. This is a result of specific binding between the antibody and F—$(CH_2)_6$—T. Antifluorescein 4-4-20 is a high affinity antibody for fluorescein ($K_d$~$10^{10}$ M). When it binds to fluorescein in the F—$(CH_2)_6$—T conjugate, the intramolecular monomer⇌dimer equilibrium is driven towards the monomer side because the active site can not accommodate both fluorophores. This structural change causes significant increase in fluorescence intensity because of the intramolecular dimer dissociation. It is important to note, however, that only the fluorescence of rhodamine ($\lambda_{max}$=576 nm) is enhanced, and that of fluorescein ($\lambda_{max}$=515 nm) remains low and constant. This observation may be attributed to two factors. First is the resonance energy transfer (RET) from F to T. The efficiency of RET is proportional to the inverse 6th power of the distance between donor and acceptor molecules. Because the maximal distance between F and T in the conjugate is ~10 Å, the transfer efficiency is almost 100%, suggesting that the excited-state energy of F may be completely transferred to T. Second is the high degree of quenching in the antibody active site. It is well known that 4-4-20 quenches fluorescein fluorescence by 96% upon binding due to interactions with active site residues. These quenching effects for fluorescein are in many cases desirable because they produce a large effective Stoke's shift for the F—$(CH_2)_n$—T conjugates. The conjugates can be excited at 488 nm (a common laser line) and emit at ~$\lambda_{max}$=580 nm. This property enables the rejection of background interference due to light scattering or endogenous fluorescence in biological samples.

enhancement factor (E) as a function of antibody concentration for the four conjugates. In the second experiment, 4-4-20 solutions of fixed concentration (~$10^{-8}$ M) were titrated with aliquots of stock F—$(CH_2)_n$—T solution. Fluorescence intensities thus obtained were analyzed according to method II. FIG. 23 shows the enhancement factor (E) as a function of F—$(CH_2)_n$—T concentration for the four conjugates. Values of dissociation constant ($K_d$) and maximum enhancement factor at 589 nm $E_m^{589}$ are summarized in Table 2 and plotted in FIG. 24. The results show that as the linker becomes longer, the binding affinity increases while the fluorescence enhancement decreases.

TABLE 2

Figure 20:
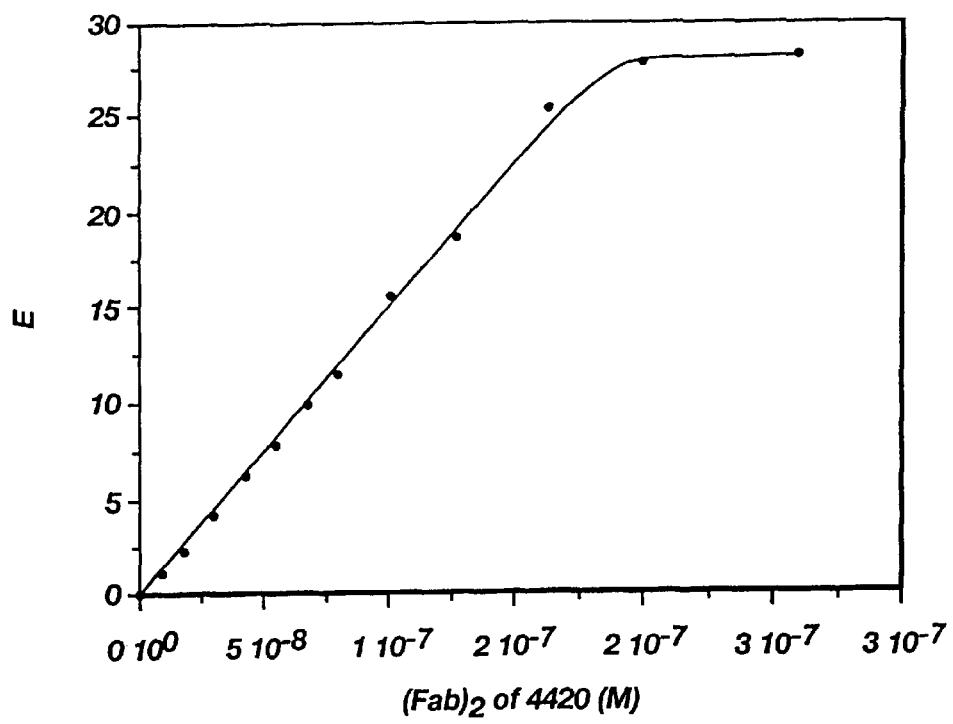
FIG. 20 is a graph depicting fluorescence enhancement factor (E) calculated from intensities at 576 nm ($\lambda_{max}$) in FIG. 19 as a function of (Fab')$_2$ concentration ($P_o$) A value of $6 \times 10^{-10}$ M was obtained for $K_d$ and 28.5.

Summary of binding parameters obtained in FIG. 20

| | Dissociation constant $K_d$ (nM) | | | | Maximal Enhancement Factor ($E_m^{589}$) | | | |
|---|---|---|---|---|---|---|---|---|
| Compound | I (n = 2) | II (n = 4) | III (n = 6) | IV (n = 8) | I (n = 2) | II (n = 4) | III (n = 6) | IV (n = 8) |
| Method I | 1.3 | 3.4 | 1.0 | 0.6 | 114.6 | 108.4 | 41.8 | 26.2 |
| Method II | 5.0 | 2.6 | 0.7 | N/A | 109.9 | 95.5 | 42.1 | N/A |
| Average | 3.2 | 3.0 | 0.9 | 0.6 | 112.3 | 102.0 | 42.0 | 26.2 |

FIG. 20 is a plot of fluorescence enhancement (E), calculated from the intensity values at the emission maximum (575 nm), vs (Fab')$_2$ concentration ($P_o$) This data set was fit to eq 3. The maximum enhancement ($E_m$) was found to be 28.5 and the dissociation constant ($K_d$) was $6 \times 10^{-10}$ M. The value of $K_d$ is slightly higher than that for free fluorescein (~$10^{-10}$ M) because a small portion of the binding free energy was devoted to dissociate the F and T heterodimer which have $K_d$ values of ~$10^{-2}$ to $10^{-3}$ M. It should be pointed out that the magnitude of fluorescence enhancement (~30-fold) is exceptional and unparalleled by other comparable systems involving fluorescent immunoreactions. In most RET-based methods reported in the literature, it is the donor fluorescence that is modulated, rather than that of the acceptor. Stryer et al. *Proc. Natl. Acad. Sci. USA* 58:719–726 (1967); Ullman et al. *Methods in Enzymology,* 74: 28–60 (1981). In some cases, the binding-mediated intensity changes are very marginal. Barnard et al. *Science,* 251: 927–929 (1991).

Figure 21:
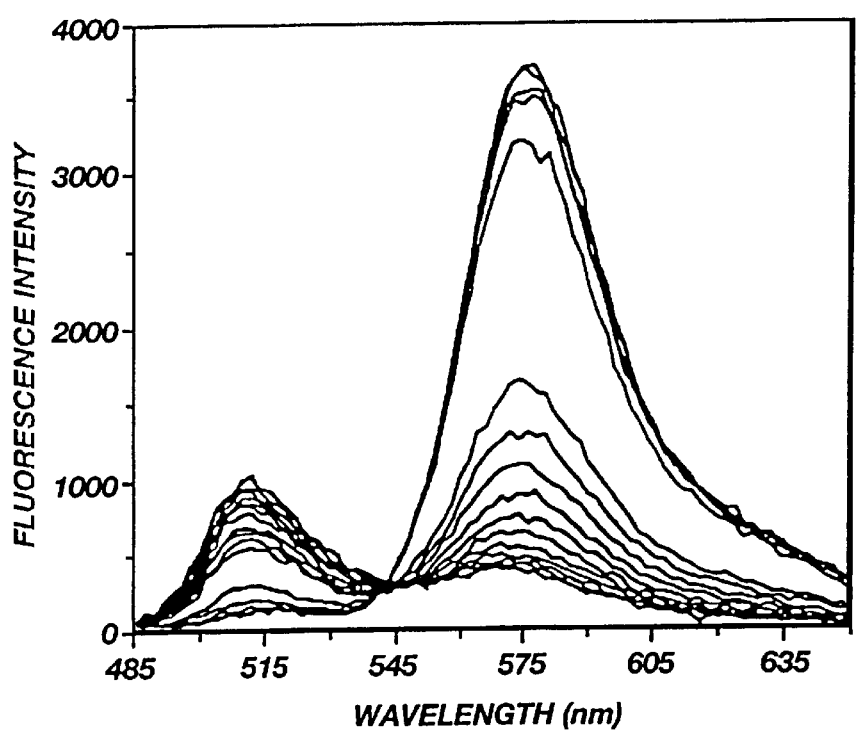
FIG. 21 is a graph depicting technical fluorescence spectra of F—$(CH_2)_6$—T (V) ($4.2 \times 10^{-7}$ M) in the presence of 4-4-20 (Fab')$_2$ ($2.6 \times 10^{-7}$ M) as 10 ml aliquots of 5-aminofluorescein (AF) solution were added. The total AF concentration varied from zero to $6.2 \times 10^{-7}$ M. Spectra measured after 2 and 30 min were completely superimposable, indicating that exchange equilibrium was achieved in a period of less than 2 min. Experimental conditions are the same as in FIG. 18.

The reversibility of the antibody-mediated fluorescence enhancement was examined by titrating a mixture of 4-4-20 and F—$(CH_2)_6$—T with 5-aminofluorescein which is a nonfluorescent analog of fluorescein. Spectra shown in FIG. 21 demonstrate that rhodamine fluorescence ($\lambda_{max}$=576 nm) decreases with increasing concentration of 5-aminofluorescein. The slight increase at ~515 nm is attributed to the residual fluorescence of 5-aminofluorescein itself. This experiment indicates that F—$(CH_2)_6$—T can be displaced from antibody sites into its quenched state again. BSA and mouse IgG had no effect on the fluorescence intensity of F—$(CH_2)_6$—T in either bound or unbound states. These results indicate that the fluorescence enhancement observed was indeed specific and reversible.

Dependence on Linker Length

Figure 22:
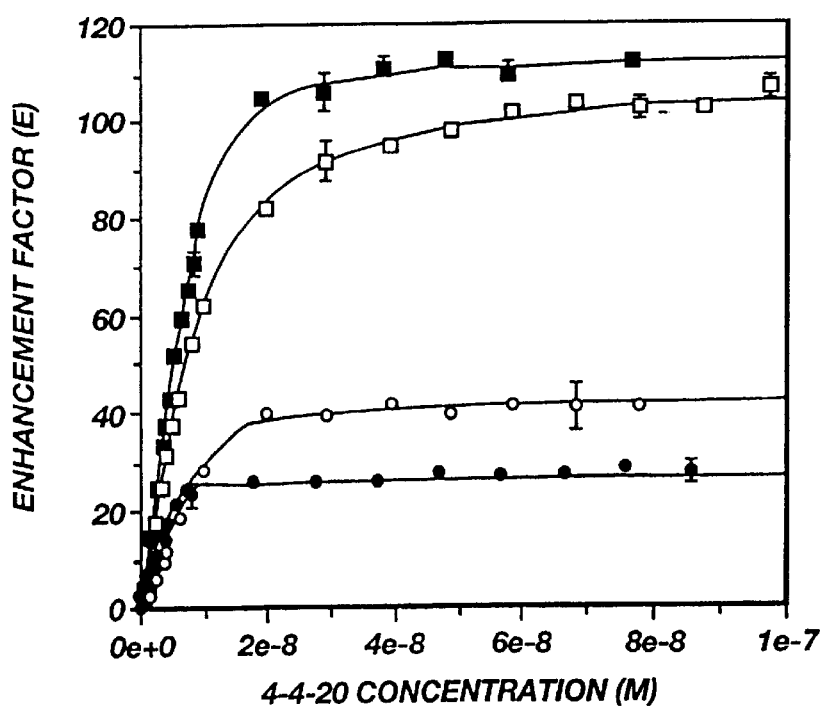
FIG. 22 is a graph depicting fluorescence enhancement factor (E) at 589 nm as a function of 4-4-20 (intact IgG) concentration ($P_o$) for conjugates I (n=2, filled squares), II (n=4, open squares), III (n=6, open circles) and IV (n=8, filled circles). The maximal enhancement factor ($E^{m589}$) was found to be 114.6, 108.4, 41.8 and 26.2, respectively. The data were derived from titrating a solution of each F—$(CH_2)_n$—T conjugate (~$10^{-8}$ M) with 5 ml aliquots of a stock 4-4-20 solution. Fluorescence intensities were measured at 589 nm with Ex=488 nm. Other experimental conditions are the same as in FIG. 18.

Four conjugates with n=2, 4, 6, 8 were studied in order to examine the effect of linker length on the binding properties of F—$(CH_2)_n$—T. In the first experiment, F—$(CH_2)_n$—T solutions of fixed concentration (~$10^{-8}$M) were titrated with aliquots of stock 4-4-20 solution. Fluorescence intensities thus obtained were analyzed according to method I described in Materials and Methods. FIG. 22 shows the The excited-state energy of one rhodarine molecule can be transferred efficiently to another at a proximity of <50 Å. This is a resonance energy transfer process that can occur through space without the need for physical contact between the donor and acceptor molecules. Because both factors are distance-dependent, a longer linker would have more flexibility and can bring two rhodamine molecules closer together. For this reason, the fluorescence enhancement factor decreases as the linker gets longer. Apart from the above explanations, two other trivial factors may also contribute to the observed linker effect on $E_m^{589}$. First, a longer linker has a higher degree of conformational freedom which may reduce the stacking efficiency between F and T. Because of this, the level of background fluorescence ($I_b$) may be elevated. According to the definition of E (eq 2), a higher $I_b$ would correspond to a lower $E_m^{589}$. However, control experiments showed little difference in background fluorescence among the four conjugates, indicating this is probably a trivial factor. Second, a longer linker may allow rhodamine molecules to fold up and remain associated with fluorescein even when the latter is bound to its antibody. However, examination of the 3-dimensional structure of the 4-4-20 Fab-fluorescein complex reveals that the size, geometry and residue positioning of the active site are all tailored to bind with fluorescein. Herron et al. *Proteins: Structure, Function and Genetics,* 5:271–280 (1989). It is unlikely that both fluorophores can be accommodated in the active site. Although dynamic interactions of rhodamine with neighboring residues may quench some of its fluorescence, this is probably also a trivial factor because such dynamic quenching should occur for all linkers.

Effect of Linking Chemistry

All conjugates discussed so far employ isothiocyanate chemistry for linkages between fluorophores and the alkyl chains. However, thiourea bonds are known to be labile and can result in significant chemical dislocation especially after long-term storage. For this reason, we decided to introduce amide chemistry into one of the conjugates (n=6) to prepare F—$(CH_2)_6$—T (VI). Its spectral and binding properties were compared to those of F—$(CH_2)_6$—T (III). Although the changes in chemistry are small, they do have profound effect on its properties. In the first experiment, fluorescence spectra of F—(CH$_2$)$_6$—T (VI) (3×10$^{-7}$ M) were measured when aliquots of 4-4-20 solution were added. Results are shown in FIG. 25. When unbound, the conjugate has a predominant peak from fluorescein and a shoulder peak due to rhodamine. Binding to 4-4-20 provides a flip-flop in the relative intensities of F and T. The decrease in fluorescein fluorescence is attributed to binding-associated quenching in the active site, while the increase in rhodamine fluorescence is a result of dissociation of the intramolecular hetero-dimers between F and T. These results indicate that both conjugates exhibit similar properties in terms of binding-mediated modulation of rhodamine fluorescence. However, the amide chemistry causes incomplete quenching of fluorescein fluorescence in the free state, presumably, due to inefficient stacking and/or improper orientation alignment between the two fluorophores.

Figure 15:
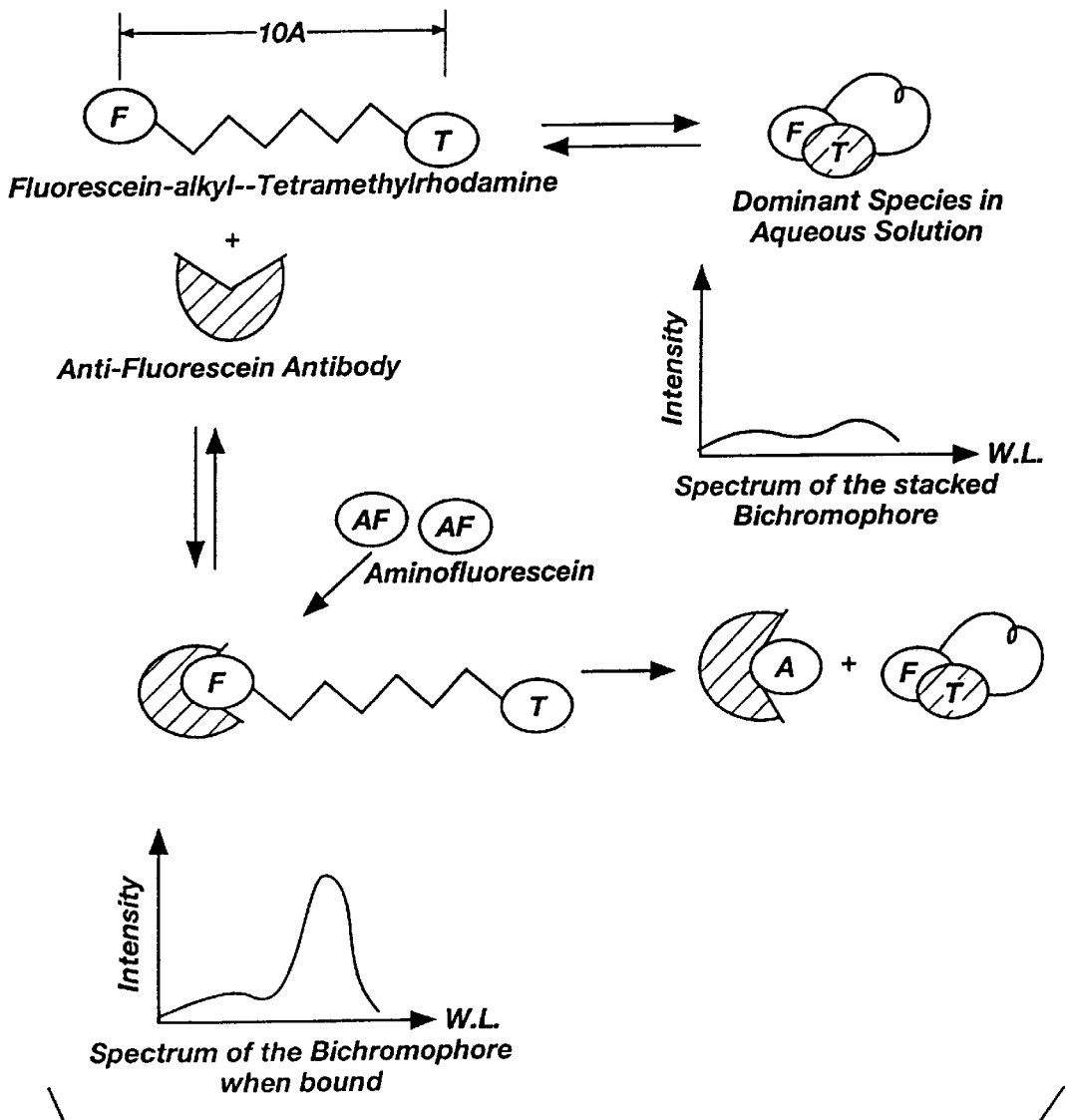
FIG. 15 is a schematic illustration of an embodiment of the invention of using antifluorescein antibodies (anti-F) to modulate rhodamine fluorescence. Fluorescein (F) and tetramethylrhodamine (T) are chemically linked via a short alkyl spacer. Binding of anti-F to this bichromophoric conjugate drives the intramolecular dimer-monomer equilibrium towards the monomer side, which results in a concomitant increase in rhodamine fluorescence. This process is specific and can be reversed by the addition of fluorescein and its analogs such as 5-aminofluorescein (AF).

In the second experiment, we were interested in a more quantitative comparison of differences in binding affinity and enhancement factors. A typical titration curve was obtained by titrating a F—(CH$_2$)$_6$—T (VI) solution of fixed concentration (1.8×10$^{-7}$ M) with aliquots of 4-4-20 solution (FIG. 26). The E~P$_o$ data set was fit to eq 3, giving a value of 5×10$^{-7}$ M for K$_d$ and 24.8 for E$_m^{589}$. The nearly 25-fold fluorescence enhancement was specific to 4-4-20 and can be reversed by the addition of 5-aminofluorescein. This enhancement value is comparable to those obtained in FIG. 17 and FIG. 20, although slightly lower in magnitude. A more significant difference is in the value of K$_d$—about 500-fold lower than that shown in Table 2 (Kd=0.9 nM for n=6). Conjugates with the thiourea linkage can bind better because their structures more closely mimic the original immunogen in which fluorescein was linked to the side chain of lysine residues of a carrier protein via the thiourea bond. Although both conjugates VI and III have six CH$_2$ units in their linker, VI is two bonds shorter than the latter (measured from 5C of F to 5C of T, see FIG. 15) because of , different linking chemistry. As discussed earlier, shorter linkers tend to reduce binding affinity because of steric hindrances. In addition, a more fundamental explanation may be found by examining the two linkages:

where Ar stands for an aromatic ring. In the amide bond, the Ar—C bond is rotable and O, C, N atoms are co-planar due to electron delocalization. In the thiourea bond, however, there are no rotable bonds and Ar, N, C, S, N are all co-planar. Because intramolecular dimerlization requires F and T to fold upon each other, bond rotation and flexibility are necessary conditions for the formation of tight dimers. Therefore, we can reasonably conclude that F and T are more efficiently stacked when amide chemistry is used. Supporting this conclusion is the diminished affinity of F—(CH$_2$)$_6$—T (VI) with another antifluorescein antibody 9–40 which comes from the same gene family as 4-4-20 but has lower affinity toward fluorescein (K$_a$~10$^7$ M$^{-1}$).

Polarization Spectra

Figure 27:
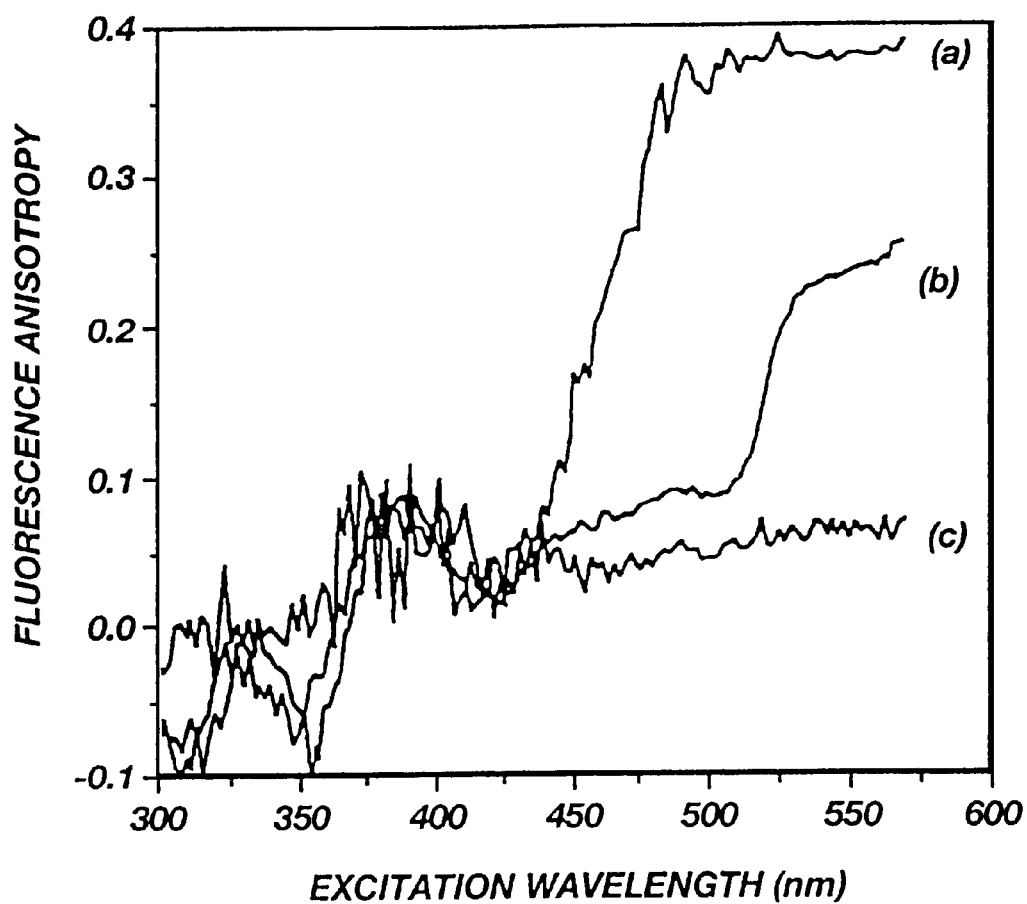
FIG. 27 is a graph depicting fluorescence polarizadon spectra of F—$(CH_2)_6$—T (VI) in the absence (c) and presence (b) of 4-4-20 are compared to that of rhodamine bound to an antirhodamine antibody (a).

The bright rhodamine fluorescence observed for the bound bichromophores may result from two mechanisms: direct excitation of the rhodamine oscillator at 488 nm after de-quenching by binding and/or resonance energy transfer (RET) from F to T. Although both mechanisms are possible, RET probably dominates the process. Control experiments showed that the fluorescence intensity of monomeric rhodamine is less than 10% of the level observed for the bound F—(CH$_2$)$_6$—T (VI) conjugate when excited at 488 nm. This indicates that because of the weak oscillator strength at this wavelength, direct excitation only accounts for a small portion of the observed enhancement of rhodamine fluorescence. The majority is contributed by the excited-state energy transfer process. This is best illustrated by the result in FIG. 27 which shows the fluorescence polarization spectra of free and bound F—(CH$_2$)$_6$—T (VI) conjugate in comparison with that of a rhodamine molecule bound to an antirhodamine antibody. The wavelength at which the major polarization transition occurs is shifted from ~450 nm for the bound rhodatnine to ~525 nm for the bound F—(CH$_2$)$_6$—T (VI). This suggests that there is an additional dipole which, although not intrinsically present in the rhodamine molecule, can still relax from its excited state into the lowest singlet state of the rhodamine emission dipole. The new dipole is clearly introduced by the presence of fluorescein. This is, in fact, a consequence of the Forster energy transfer theory. It should be noted that the excitation dipole of fluorescein and the emission dipole of rhodamine are not coplanar. Also, the fact that the anisotropy value of the bichromophore does not level off at the maximal value of 0.4 (as found for antibody-bound rhodamine) suggests that there is significant depolarization effect. This demonstrates that rhodamine has higher rotational freedom when linked to antibody-bound fluorescein than when itself is bound to an antibody In summary, we have demonstrated that the fluorescence emission of tetramethylrhodamine (T) can be modulated by antibodies that are highly specific to fluorescein (F) and do not cross-react with T. This is achieved by conjugating F and T via an oligomethylene spacer to make a so called bichromophore. Due to the short interchromophore distance, F and T can fold upon each other to form stacked intramolecular hetero-dimers. As a result, both fluorophores are essentially non-fluorescent. However, when an antifluorescein antibody binds to the fluorescein moiety of the bichromophore, the dynamic monomerxdimer equilibrium is driven towards the monomeric form which is highly fluorescent. Therefore, the fluorescence emission is effectively coupled to the antibody-ligand binding events. As an added advantage, this system makes use of the resonance energy transfer properties between F and T so that the excited-state energy of fluorescein can be transferred nonradiatively to rhodamine which in turn emits its own fluorescence. In effect, the bichromophore is a molecule with a long Stoke's shift whose fluorescence emission can be modulated by binding to antibodies. This combinatorial use of fluorescent dye dimerization and fluorescence energy transfer is novel and unique, especially in the context of coupling these phenomena to biomolecular binding events.

The implications of this study can be seen from several perspectives. First, antifluorescein antibodies quench ligand fluorescence upon binding. This property provides a convenient means to measure binding parameters in research laboratories. However, quenching is not always desirably in some experiments (e.g. polarization measurements) because the bound species contribute little to the total fluorescence intensity. This disadvantage can be offset by introducing fluorescence enhancement into the system. Enhancement combined with the long Stoke's shift will also help expand the applications of the antifluorescein system from laboratory use into practical areas such as biosensors, Wei et al. *Biosensor Design and Application,* 511:105–120 (American Chemical Society, Washington D.C. 1992) clinical immunoassays, Wei et al. *Anal. Chem.,* 66:1500–1506

Figure 14:
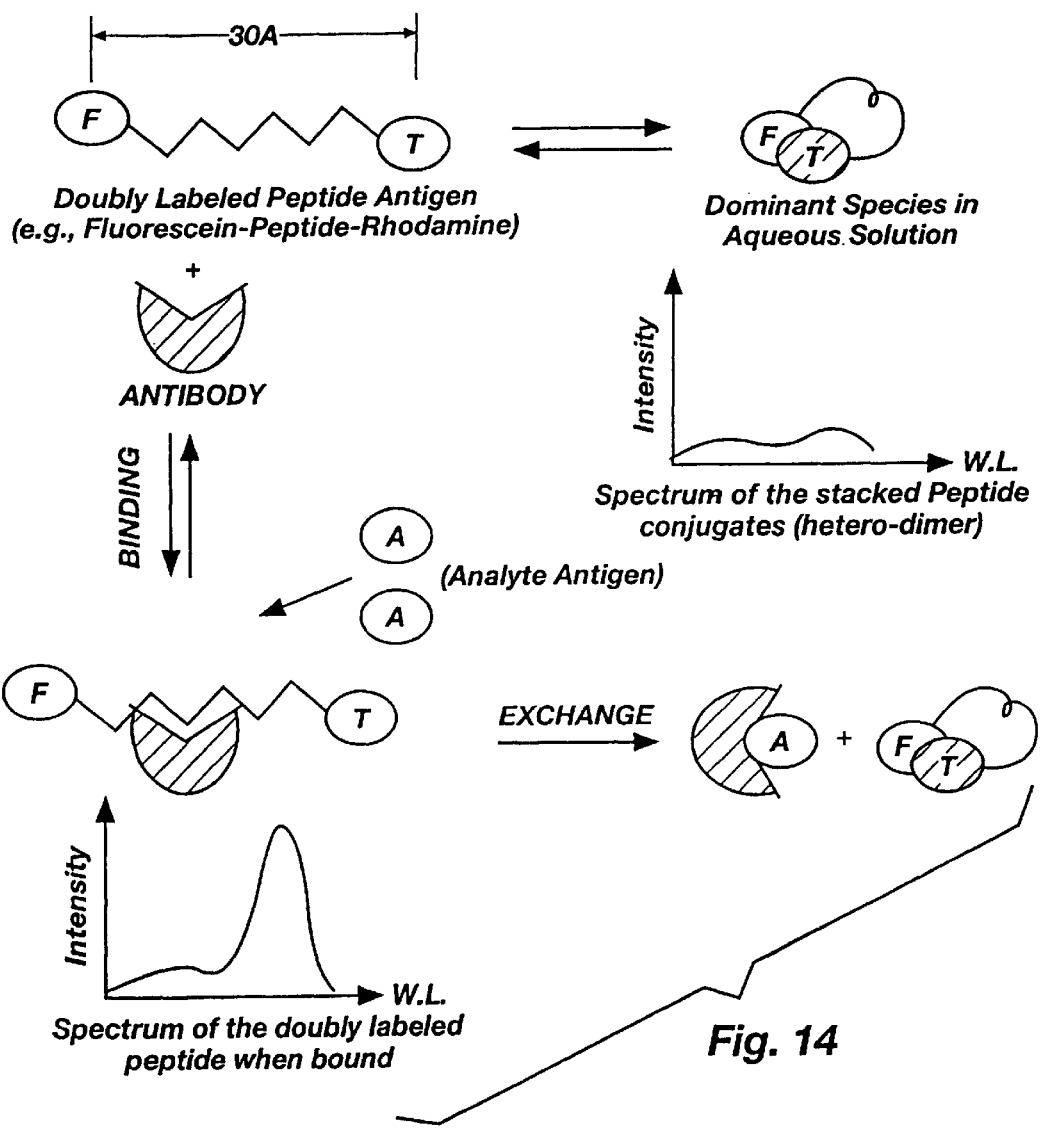
FIG. 14 schematically represents an embodiment of the invention.

(1994) fluorescence activated cell sorters Karawajew et al. *J. Immunol. Methods,* 111:95–99 (1988) and characterization of liposomal vesicles. Second, the concept described herein (see FIGS. 14 and 15) is not limited to the antifluorescein model system. The fact that similar results were obtained with two different systems (e.g. hCG and antifluorescein) involving both high and low molecular antigens suggest that the concept is quite general. This is important because our approach for the first time combines fluorescent detection with molecular recognition—two events which were usually separated in most other systems. Wei et al. (1992) supra. Third, the magnitude of antibody-mediated fluorescence enhancement found in this study is phenomenal—up to 110-fold depending upon the linker length. This can be used as a model to improve other systems and to understand the fundamental biophysical mechanisms behind it.

EXAMPLE

A homogenous DNA hybridization assay in which a pair of fluorophores (fluorescein and rhodamine) is attached to the 5' and 3' ends, respectively, of an oligonucleotide (30 nucleotides in length) which is complementary to a target DNA sequence that is part of a much larger piece of DNA (chromosomal DNA). The flourescently-labeled oligonucleotide is mixed with the target DNA and the mixture heated to a temperature high enough to denature the double helix. As the mixture cools, the oligonucleotide hybridizes with its target sequence. The unbound form of the fluorescently labeled oligonucleotide is non-fluorescent because of dimer formation between the two dyes. Upon hybridization however, this dimer dissociates, resulting in an increase in fluorescence. As such, this is a homogenous, solution phase assay because no wash steps are required. Its sensitivity would be limited, however, by the sensitivity of the fluorometer for bulk fluorescence (e.g. one picomolar would be a practical limit with current instrumentation).

EXAMPLE

The experiment of the previous EXAMPLE is repeated somewhat to produce a solution-phase homogenous RNA hybridization assay in which a pair of fluorophores (Cy-3 and Cy-5) is attached to the 5' and 3' ends, respectively of an oligonucleotide (10 nucleotides in length) which is complementary to a target RNA sequence that is part of a larger piece of RNA. The target RNA is denatured first, for example by heating it to a temperature high enough to denature the double helix, at which point the flourescently-labeled oligonucleotide is added and then mixed with the target RNA. As the mixture cools, the oligonucleotide would hybridize with its target sequence. The unbound form of the fluorescently labeled oligonucleotide is non-fluorescent because of dimer formation between the two dyes. Upon hybridization however, the dimer dissociates, resulting in an increase i fluorescence. As such, this too is a homogenous, solution phase assay because no wash steps are required.

The EXAMPLES were provided to illustrate certain embodiments of the present invention and, for that reason, should not be construed in a limiting sense.

We claim:
1. A procedure for detecting and quantifying a first DNA in bulk solution comprising:
(a) placing in the bulk solution a conjugate comprising: a second DNA strand complementary to at least a portion of said first DNA, said second DNA strand having a pair of fluorescent materials capable of forming a dimer joined thereto with sufficient nucleotides between said pair of fluorescent materials so the second DNA strand is capable of folding upon itself, said conjugate capable of moving between a more stacked configuration and a more stacked configuration to exhibit a change in fluorescence; and
(b) adding the first DNA to the bulk solution to bind with the conjugate to alter the configuration of the pair of fluorescent materials and alter the fluorescence of the fluorescent materials to detect and quantify the first DNA.

2. The procedure of claim 1 wherein said fluorescent materials are fluorescent energy transfer dyes.

3. The procedure of claim 1 wherein said fluorescent materials are organic ligands of lanthanide metals.

4. The procedure of claim 1 wherein the fluorescent materials are attached to the 3' and 5' ends of the second DNA.

5. A procedure for detecting and quantifying a first DNA in bulk solution comprising:

(a) placing in the bulk solution a conjugate comprising: a second DNA strand complementary to at least a portion of said first DNA, said second DNA strand having a pair of fluorescent materials capable of forming a dimer attached to the ends of the second DNA strand, said conjugate capable of moving between a more stacked configuration and a more stacked configuration to exhibit a change in fluorescence; and (b) adding the first DNA to the bulk solution to bind with the conjugate to thus alter the configuration of the pair of fluorescent materials and alter the fluorescence of the fluorescent materials in order to detect and quantify the first DNA.

6. The process of claim 5 wherein said fluorescent materials are fluorescent energy transfer dyes.

7. The process of claim 5 wherein said fluorescent materials are organic ligands of lanthanide metals.

* * * * *

SEQUENCE LISTING

```
(1) GENERAL INFORMATION:

(iii) NUMBER OF SEQUENCES:2

(2) INFORMATION FOR SEQ ID NO:1:

(i) SEQUENCE CHARACTERISTICS:
        (A) LENGTH:7 amino acids
        (B) TYPE:amino acid
        (D) TOPOLOGY:linear (xi) SEQUENCE DESCRIPTION:SEQ ID NO:1:

Arg Leu Pro Gly Pro Ser Asp
      1               5

(2) INFORMATION FOR SEQ ID NO:2:

(i) SEQUENCE CHARACTERISTICS:
        (A) LENGTH:13 amino acids
        (B) TYPE:amino acid
        (D) TOPOLOGY:linear (xi) SEQUENCE DESCRIPTION:SEQ ID NO:2:

Gly Ser Gly Ser Arg Leu Pro Gly Pro Ser Asp Thr Cys
              1               5                 10
```